US012042564B2

(12) United States Patent
Rands et al.

(10) Patent No.: US 12,042,564 B2
(45) Date of Patent: *Jul. 23, 2024

(54) THERAPEUTIC SOLID DOSAGE FORMS

(71) Applicant: CYBIN UK LTD, London (GB)

(72) Inventors: Peter Rands, London (GB); Tiffanie Benway, London (GB); Zelah Joel, London (GB); Marie Layzell, London (GB); Ellen James, London (GB)

(73) Assignee: CYBIN UK LTD, London (GB)

( * ) Notice: Subject to any disclaimer, the term of this patent is extended or adjusted under 35 U.S.C. 154(b) by 232 days.

This patent is subject to a terminal disclaimer.

(21) Appl. No.: 17/320,155

(22) Filed: May 13, 2021

(65) Prior Publication Data

US 2021/0378969 A1 Dec. 9, 2021

(30) Foreign Application Priority Data

| Jun. 2, 2020 | (GB) | 2008303 |
| Jun. 2, 2020 | (WO) | PCT/EP2020/065244 |
| Dec. 1, 2020 | (GB) | 2018950 |
| Dec. 1, 2020 | (GB) | 2018955 |
| Mar. 22, 2021 | (GB) | 2103981 |
| Apr. 23, 2021 | (WO) | PCT/EP2021/060750 |

(51) Int. Cl.
| A61K 31/4045 | (2006.01) |
| A61K 9/00 | (2006.01) |
| A61K 9/20 | (2006.01) |
| A61K 9/48 | (2006.01) |
| A61K 9/50 | (2006.01) |
| C07B 59/00 | (2006.01) |
| C07D 209/16 | (2006.01) |

(52) U.S. Cl.
CPC ............ *A61K 9/485* (2013.01); *A61K 9/0053* (2013.01); *A61K 9/2009* (2013.01); *A61K 9/2013* (2013.01); *A61K 9/2027* (2013.01); *A61K 9/2054* (2013.01); *A61K 9/2059* (2013.01); *A61K 9/4858* (2013.01); *A61K 9/4866* (2013.01); *A61K 9/5057* (2013.01); *A61K 31/4045* (2013.01); *C07B 59/002* (2013.01); *C07D 209/16* (2013.01); *C07B 2200/05* (2013.01)

(58) Field of Classification Search
CPC ..... A61K 31/405; A61K 31/407; A61K 31/41
See application file for complete search history.

(56) References Cited

U.S. PATENT DOCUMENTS

| 4,336,378 A | 6/1982 | Brand et al. |
| 8,268,856 B2 | 9/2012 | Hamann et al. |
| 11,000,534 B1 | 5/2021 | Sippy |
| 11,242,318 B2 | 2/2022 | Nivorozhkin et al. |
| 11,406,619 B2 | 8/2022 | Layzell et al. |
| 11,471,417 B2 * | 10/2022 | Rands ................ A61K 9/4866 |
| 11,578,039 B2 | 2/2023 | Rands et al. |
| 11,643,390 B2 | 5/2023 | Rands et al. |
| 11,660,289 B2 | 5/2023 | Rands et al. |
| 11,697,638 B2 | 7/2023 | Rands et al. |
| 11,773,062 B2 | 10/2023 | Rands et al. |
| 2002/0022667 A1 | 2/2002 | Pace et al. |
| 2009/0076121 A1 | 3/2009 | Czarnik et al. |
| 2018/0221396 A1 | 8/2018 | Chadeayne |
| 2020/0339519 A1 | 10/2020 | Kim et al. |
| 2020/0390746 A1 | 12/2020 | Rands et al. |
| 2021/0395201 A1 | 12/2021 | Rands et al. |
| 2021/0403426 A1 | 12/2021 | Rands et al. |
| 2022/0062237 A1 | 3/2022 | Layzell et al. |
| 2022/0062238 A1 | 3/2022 | Ayzell et al. |
| 2022/0081396 A1 | 3/2022 | Rands et al. |
| 2022/0281818 A1 | 9/2022 | Rands et al. |
| 2022/0313660 A1 | 10/2022 | Layzell et al. |
| 2023/0086574 A1 | 3/2023 | Rands et al. |
| 2023/0149293 A1 | 5/2023 | Rands et al. |
| 2023/0167056 A1 | 6/2023 | Rands et al. |
| 2023/0181530 A1 | 6/2023 | Rands et al. |
| 2023/0250059 A1 | 8/2023 | Rands et al. |
| 2024/0016782 A1 | 1/2024 | Rands et al. |

FOREIGN PATENT DOCUMENTS

| GB | 2585978 A | 1/2021 |
| GB | 2586940 A | 3/2021 |
| GB | 2596884 A | 1/2022 |
| WO | WO 02-083144 A1 | 10/2002 |
| WO | 2004085392 A1 | 10/2004 |
| WO | WO 2008-049116 A2 | 4/2008 |
| WO | 2008071455 A1 | 6/2008 |

(Continued)

OTHER PUBLICATIONS

Barker et al., "Metabolism of the Hallucinogen N,N-Dimethyltryptamine in Rat Brain Homogenates", Biochemical Pharmacology, vol. 29, pp. 1049-1057. 1980.
Rands et al., Unpublished U.S. Appl. No. 18/193,866, filed Mar. 31, 2023.
Rands et al., Unpublished U.S. Appl. No. 18/152,465, filed Jan. 10, 2023.
Rands et al., Unpublished U.S. Appl. No. 18/056,771, filed Nov. 18, 2022.
Rands et al., Unpublished U.S. Appl. No. 18/163,388, filed Feb. 2, 2023.
Rands et al., Unpublished U.S. Appl. No. 17/616,345, filed Dec. 3, 2021.
Rands et al., Unpublished U.S. Appl. No. 17/469,063, filed Sep. 8, 2021.
Rands et al., Unpublished U.S. Appl. No. 17/574,424, filed Jan. 12, 2022.

(Continued)

*Primary Examiner* — Micah Paul Young
(74) *Attorney, Agent, or Firm* — Heslin Rothenberg Farley & Mesiti P.C.

(57) ABSTRACT

The present invention relates to a solid dosage form comprising two or more compounds selected from N,N-dimethyltryptamine and its deuterated analogues and pharmaceutically acceptable salts thereof, and methods of treatment (e.g., of a psychiatric disorder or a neurological disorder) comprising administering the solid dosage form to a patient in need thereof.

21 Claims, 5 Drawing Sheets

(56) References Cited

FOREIGN PATENT DOCUMENTS

| | | | |
|---|---|---|---|
| WO | 2009049030 A1 | 4/2009 | |
| WO | 2018195455 A1 | 4/2009 | |
| WO | 2020169850 A1 | 10/2018 | |
| WO | WO 2019-081764 A1 | 5/2019 | |
| WO | WO-2019081764 A1 * | 5/2019 | ......... A61K 31/4045 |
| WO | 2020169851 A1 | 8/2020 | |
| WO | 2020-176597 A1 | 9/2020 | |
| WO | 2020-176599 A1 | 9/2020 | |
| WO | WO 2020-245133 A1 | 12/2020 | |
| WO | WO 2021-089872 A1 | 5/2021 | |
| WO | WO 2021-089873 A1 | 5/2021 | |
| WO | 2021116503 A2 | 6/2021 | |
| WO | 2021155470 A1 | 8/2021 | |
| WO | 2021234608 A1 | 11/2021 | |
| WO | 2021244831 A1 | 12/2021 | |
| WO | 2022031566 A1 | 2/2022 | |
| WO | 2022043227 A1 | 3/2022 | |
| WO | 2022069690 A2 | 4/2022 | |
| WO | 2022117359 A1 | 6/2022 | |

OTHER PUBLICATIONS

Rands et al., Unpublished U.S. Appl. No. 17/680,411, filed Feb. 25, 2022.
Brito-Da-Costa et al. "Toxicokinetics and Toxicodynamics of Ayahuasca Alkaloids N,N-Dimethyltryptamine (DMT), Harmine, Harmaline and Tetrahydroharmine: Clinical and Forensic Impact", Pharmaceuticals, vol. 13, No. 334, 36 pages. Oct. 23, 2020.
Cameron, et el., "Effects of N,N-Dimethyltryptamine on Rat Behaviors Relevant to Anxiety and Depression", ACS Chemical Neuroscience, 2018, 18 pages, 2018.
Celik, et al., "Binding of Serotonin to the Human Serotonin Transporter. Molecular Modeling and Experimental Validation", Mar. 2008.
Celik, et al., "Supplementary Information to Binding of Serotonin to the Human Serotonin Transporter. Molecular Modeling and Experimental Validation", Journal of the American Chemical Society, Mar. 2008, 14 pages.
Dunlap, et al., "Identification of Psychoplastogentic N,N-Dimethylaminoisotryptamine (isoDMT) Analogues through Structure—Activity Relationship Studies", Journal of Medicinal Chemistry, 2020, 14 pages.
Gaujac, et al., Investigations into the polymorphic properties of N,N-dimethyltryptamine by X-ray diffraction and differential scanning calorimetry, Microchemical Journal, 2013, 26 pages, 2013.
Halberstadt, et al., "Behavorial effects of x,x,B,B-tetradeutero-5-MeO-DMT in rats: comparison with 5-MeO-DMT administered in combination with a monoamine oxidase inhibitor", Psychopharmacology, Jan. 6, 2012.
Ibrahim, et al., "Marine inspired 2-(5-Halo-1H-indol-3-yl)-N,N-dimethylethanamines as Modulators of Serotonin Receptors: An Example Illustrating the Power of Bromine as Part of the Uniquely Marine Chemical Space", Marine drugs, 2017, 14 pages.
Riga, et al., The serotonin hallucinogen 5-MeO-DMT alters corticothalamic activity in freely moving mice: Regionally-selective incolovement of 5-HT1A and 5-HT2A receptors, Neuropharmacology, 2017, 12 pages.
Sard, et al., "SAR of psilocybin analogs: Discovery of a selective 5-HT2c agonist", Bioorganic & Medicinal Chemistry Letters 15, 2005, 5 pages.
Strassman, et al., "Dose-Response Study of N, N-Dimethyltryptamine in Humans: II. Subjective Effects and Preliminary Results of a New Rating Scale", Archives of General Psychiatry, Chicago, IL, Feb. 1994, 18 pages.
Tearavarich, et al., "Microwave-Accelerated Preparation and Analytical Characterization of 5-ethoxy-N,N-dialkyl-[$\alpha,\alpha,\beta,\beta$-H(4) ]- and [$\alpha,\alpha,\beta,\beta$-D(4) ]-tryptamines", Drug Testing and Analysis, vol. 3, No. 9, Dec. 2010, pp. 597-608.
Timmins, Graham S., "Expert Opin ther Pat.", HHS Public Access, Oct. 2014, 19 Pages.
Reiff et al., "Psychedelics and Psychedelic-Assisted Psychotherapy", Am J. Psychiatry, 177:5, pp. 391-410. May 2020.
Chemieliva Pharmaceutical Product List, Order No. Cat. CC0034145.
Chemieliva Pharmaceutical Product List, Order No. Cat. CC0034141.
Roseman et al., "Quality of Acute Psychedelic Experience Predicts Therapeutic Efficacy of Psilocybin for Treatment-Resistant Depression", Frontiers in Pharmacology, vol. 8, Article 974, 10 pages. Jan. 2018.
McIlhenny,e t al., "Direct analysis of psychoactive tryptamine and harmala alkaloids in the Amazonian botanical medicine ayahuasca by liquid", Journal of Chromatography A, vol. 1216(51), 2009, 9 pages.
Queiroz, et al., "Chemical composition of the ark of Tetrapterys mucronate and Identification of Acetrylcholinesterase Inhibitory Constituents", Journal of Natural Products, vol. 77(3), 2014, 7 pages.
Servillo, et al., "Citrus Genus Plants Contain N-Methylated Tryptamine Derivatives and Their 5-Hydroxylated Forms", Journal of Agricultural and Food Chemistry, vol. 61(21), 2013, 7 pages.
Grina, eta l., "Old and New Alkaloids from Zanthoxylum arborescens", Journal of Organic Chemistry, vol. 47(13), 1982, 4 pages.
Ghosal, et al., "Indole Bases of Desmodium Gyrans", Phytochemistry (Elsevier), vol. 11(5), 1972, 2 pages.
Ambinter Screening Library, Publication Date Mar. 26, 2020, Order No. Cat. Amb33838664.
Aurora Building Blocks 2, Publication Date Feb. 27, 2020, Order No. Cat A17.921.638.
MuseChem Product List, Publication Date Apr. 21, 2020, Order No. Cat. R055190.
Barker et al., "Comparison of the brain levels of N N-Dimethyltryptamine and xxB B-Tetradeutero N, N-Dimethyltryptamine Following Intraperitoneal Injection", Biochemical Pharmacology, vol. 31, No. 15, Jan. 20, 1982, 5 pages.
Beaton et al., "A Comparison of the Behavioral Eeffects of Proteo- and Deurero-N, N-Dimethrltryptamine", Pharmacology, Biochemistry, vol. 16, No. 5, Sep. 8, 1981, 5 pages.
Brandt et al., "Microwave-accelerated synthesis of psychoactive deuterated N, N-dialkylated-tryptamines", Journal of Labelled Compounds and Radiopharmaceuticals, vol. 51, No. 14, 2008, 7 pages.
Morris Philip E Jr et a.l, "Indolealkylamine Metabolism: Synthesis of Deuterated Indolealkylamines as Metabolic Probes", Journal of Labelled Compounds and Radiopharmaceuticals, John Wiley & Sons Ltd, vol. 33, No. 6, Jan. 11, 1993, 12 pages.
Barker, et al., "N, N-Dimethyltryptamine (DMT), an Endogenous Hallucinogen: Past, Present, and Future Research to Determine Its Role and Function", Frontiers in Neuroscience, Aug. 6, 2018, 17 pages.
Dyck, et al., "Effect of Deuterium Substitution on the Disposition of Intraperitoneal Tryptamine", Biochemical Pharmacology, vol. 35, issue 17, 1986, 4 pages.
Walker, et al., "Gas Chromatographic-Mass Spectrometric Isotope Dilution Assay for N,N-Dimethyltryptamine in Human Plasma", Aug. 1972, 9 pages.
Atzrodt et al. Deuterium- and Tritium-Labelled Compounds: Applications in the Life Sciences, Angew. Chem. Int. Ed., vol. 57, pp. 1758-1784. 2018.
U.S. Appl. No. 18/252,949 to Rands et al. filed May 15, 2023.
Rands et al., Unpublished U.S. Appl. No. 18/602,171, filed Mar. 12, 2024.
Rands et al., Unpublished U.S. Appl. No. 18/711,130, filed May 17, 2024.
Rands et al. Unpublished U.S. Appl. No. 18/619,547, filed Mar. 28, 2024.

* cited by examiner

THERAPEUTIC SOLID DOSAGE FORMS

CROSS-REFERENCE TO RELATED APPLICATIONS

This application claims priority to the following applications: PCT/EP2020/065244, filed Jun. 2, 2020, GB 2008303.6, filed Jun. 2, 2020, U.S. Ser. No. 16/890,664, filed Jun. 2, 2020, GB 2018950.2, filed Dec. 1, 2020, GB 2018955.1, filed Dec. 1, 2020, U.S. Ser. No. 17/108,679, filed Dec. 1, 2020, U.S. Ser. No. 17/108,938, filed Dec. 1, 2020, GB 2103981.3, filed Mar. 22, 2021, U.S. Ser. No. 17/208,583, filed Mar. 22, 2021, and PCT/EP2021/060750, filed Apr. 23, 2021, the disclosures of which are incorporated by reference herein in their entireties.

BACKGROUND

Classical psychedelics have shown preclinical and clinical promise in treating psychiatric disorders (Carhart-Harris and Goodwin (2017), *The Therapeutic Potential of Psychedelic Drugs: Past, Present and Future*, Neuropsychopharmacology 42, 2105-2113). In particular, psilocybin has demonstrated significant improvement in a range of depression and anxiety rating scales in randomised double blind studies (Griffiths et al. (2016), *Psilocybin produces substantial and sustained decreases in depression and anxiety in patients with life-threatening cancer: a randomised double-blind trial*, Journal of Psychopharmacology 30(12), 1181-1197).

N,N-dimethyltryptamine (DMT) is also understood to hold therapeutic value as a short-acting psychedelic, however its duration of action (under 20 minutes) is so short as to limit effective therapy. Administration protocols have been developed to extend the immersive psychedelic experience of DMT (Gallimore and Strassman (2016), *A model for the application of target-controlled intravenous infusion for a prolonged immersive DMT psychedelic experience*, Frontiers in Pharmacology, 7:211). However, these protocols carry risk of toxic buildup in patients who are poor metabolisers of DMT (for further discussion see Strassman et al (1994), *Dose response study of N,N-dimethyltryptamine in humans*, Arch Gen Psychiatry 51, 85).

$\alpha,\alpha,\beta,\beta$-Tetradeutero-N,N-dimethyltryptamine is known to exhibit a kinetic isotope effect, which bestows a significant difference on its in vivo pharmacokinetic profile as compared with N,N-dimethyltryptamine. Substitution of hydrogen with a deuterium at an spa carbon centre is known to give rise to a 'kinetic isotope effect' by virtue of the difference in bond strength between a CH and a CD bond (Barker et al. (1982), *Comparison of the brain levels of N,N-dimethyltryptamine and $\alpha,\alpha,\beta,\beta$-tetradeutero-N,N-dimethyltryptamine following intraperitoneal injection*, Biochemical Pharmacology, 31(15), 2513-2516). The kinetic isotope effect is one way of engineering a DMT-based medicine with enhanced pharmacokinetics, for example extended half-life or increased oral bioavailability. Another approach includes advanced formulation techniques such as thin film technology and orally dispersible tablets, which can be used alone or in combination with the kinetic isotope effect to enhance the pharmacokinetics of DMT.

SUMMARY

The present invention is based, in part, upon the ability to apply knowledge of metabolism of N,N-dimethyltryptamine in order to modify, controllably, the pharmacokinetic profile of N,N-dimethyltryptamine, thereby permitting more flexible therapeutic application. In particular, by providing individual drug substance compositions comprising mixtures of N,N-dimethyltryptamine and deuterated N,N-dimethyltryptamine analogues, in particular N,N-dimethyltryptamine comprising at least one deuterium atom at the alpha position (i.e. attached to the carbon atom to which the dimethylamino moiety is attached) and, according to certain embodiments, one or two deuterium atoms at the beta position, the present invention provides compositions and methods which enable a finely tuned single dose to maintain a patient in full dissociation from the external world, referred to herein as 'breakthrough', for a therapeutically optimised duration without relying on infusion protocols or combination therapy with monoamine oxidase inhibitors in the clinic. The present invention provides a clinically applicable solid dosage form which reduces clinical complexity and increases clinical flexibility in the administration of DMT induced psychedelic-assisted psychotherapy.

Plasma concentrations of approximately 10 ng/ml up to approximately 60 ng/ml of the compound(s) of the solid dosage forms described herein are suitable for a sub-breakthrough psychedelic experience in patients according to embodiments of the present invention. In particular, such embodiments include solid oral dosage forms of the present invention comprising deuterated N,N-dimethyltryptamine compounds, alone or with undeuterated N,N-dimethyltryptamine, and pharmaceutically acceptable salts of these compounds.

Moreover, it is known that concentrations above 60 ng/ml will typically elicit a breakthrough psychedelic experience in a patient, which may be achieved via oral dosing with a solid oral dosage form of the present invention comprising a deuterated N,N-dimethyltryptamine compound of the present invention, in particular a compound selected from $\alpha,\alpha$-dideutero-N,N-dimethyltryptamine compounds and $\alpha$-protio, $\alpha$-deutero-N,N-dimethyltryptamine compounds, and pharmaceutically acceptable salts of these compounds.

In accordance with the invention, solid dosage forms comprising two or more compounds selected from N,N-dimethyltryptamine and deuterated N,N-dimethyltryptamine compounds, are potent therapeutic agents when used in DMT assisted therapy.

Viewed from a first aspect, therefore, the invention provides a solid dosage form comprising two or more compounds selected from N,N-dimethyltryptamine and its deuterated analogues and pharmaceutically acceptable salts thereof.

According to particular embodiments, the deuterated analogues are selected from $\alpha,\alpha$-dideutero-N,N-dimethyltryptamine compounds, and $\alpha$-protio,$\alpha$-deutero-N,N-dimethyltryptamine compounds.

In other embodiments, the deuterated analogues are deuterated analogues of DMT, which are $\alpha,\alpha$-diprotio-N,N-dimethyltryptamine compounds.

In some embodiments, the deuterated analogues are compounds of Formula I:

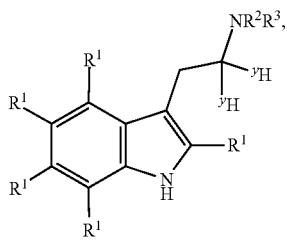

(I)

wherein:
each $R^1$ is independently selected from H and D;
$R^2$ is selected from $CH_3$ and $CD_3$;
$R^3$ is selected from $CH_3$ and $CD_3$;
each $^yH$ is independently selected from H and D; and
the ratio of deuterium:protium in a compound of Formula I is greater than that found naturally in hydrogen,
or pharmaceutically acceptable salts thereof.

In preferred embodiments, the $R^1$ moiety attached to the five-membered ring is H. In more preferred embodiments, each $R^1$ is H. In primary embodiments, both $^yH$ are D. In some primary embodiments, both $R^2$ and $R^3$ are $CD_3$ and each $R^1$ is H. In secondary embodiments, both $R^2$ and $R^3$ are $CD_3$. In some secondary embodiments, both $^yH$ are are H and each $R^1$ is H.

Particularly preferred solid dosage forms comprise one or more compounds selected from Compounds 1 to 5, or a pharmaceutically acceptable salt thereof.

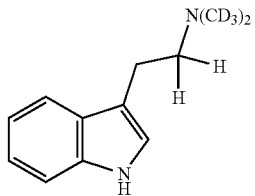

Viewed from a second aspect, the invention provides a solid dosage form as defined according to the first aspect for use in therapy, for example DMT-assisted psychotherapy.

Viewed from a third aspect, the invention provides a solid dosage form as defined according to the first aspect for use in a method of treating a psychiatric disorder or a neurological disorder in a patient.

Viewed from a fourth aspect, the invention provides a method of treating a psychiatric or neurological disorder comprising administering to a patient in need thereof a solid dosage form as defined according to the first aspect.

Viewed from a fifth aspect, the invention provides the use of a solid dosage form as defined according to any one of the first aspect in the manufacture of a medicament for use in a method of treating a psychiatric or neurological disorder in a patient.

Viewed from a sixth aspect, the invention provides a solid dosage form as defined in the first to third aspects, or the method of the fourth aspect, or the use of the fifth aspect, wherein the solid dosage form comprises a buffer. In preferred embodiments of the sixth aspect, the pH of the solid dosage form is maintained between 3.5 and 6.5.

Further aspects and embodiments of the present invention will be evident from the discussion that follows below.

DETAILED DESCRIPTION

Figure 1:
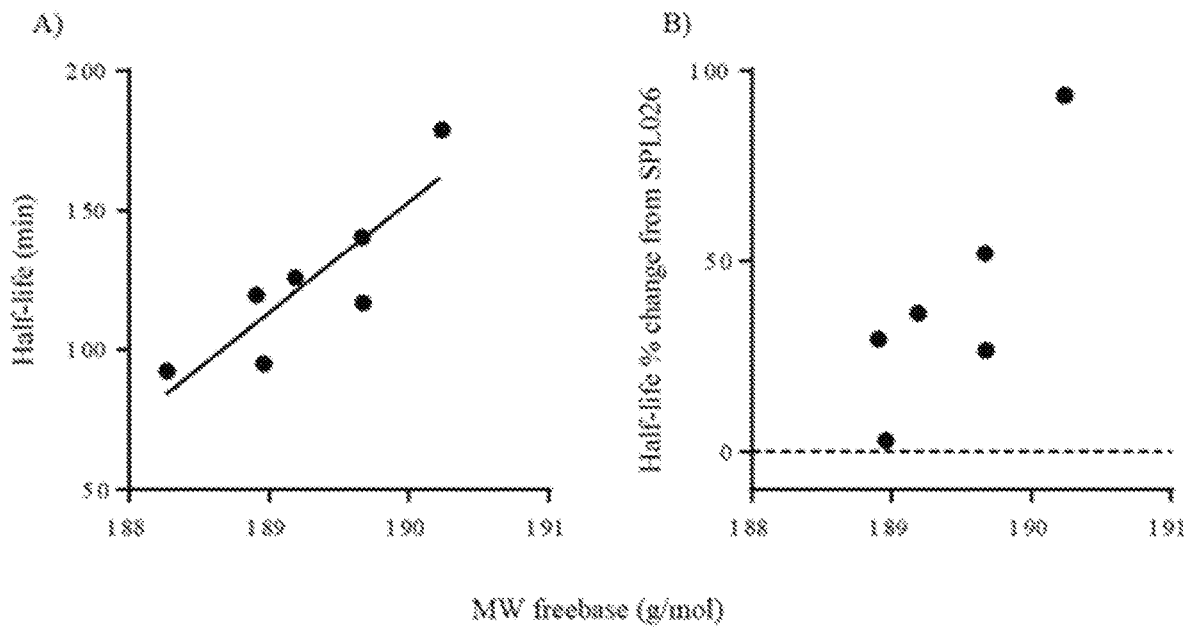
FIG. 1 plots calculated in vitro half-life for DMT and 6 deuterated-containing compositions described in Example 4. A) Linear regression analysis. The r2 value for half-life is 0.754; where the slope was found to be significantly different to zero, p=0.01. B) Half-life of deuterated analogues as a percent change from (undeuterated) DMT fumarate (dashed line).

Throughout this specification, one or more aspect of the invention may be combined with one or more features described in the specification to define distinct embodiments of the invention.

References herein to a singular of a noun encompass the plural of the noun, and vice-versa, unless the context implies otherwise.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention provides a solid dosage form comprising two or more compounds selected from N,N-dimethyltryptamine compounds, for example α,α-dideutero-N,N-dimethyltryptamine compounds, α-protio, α-deutero-N,N-dimethyltryptamine compounds and pharmaceutically acceptable salts of these compounds.

A protium atom (H) is a hydrogen atom with zero neutrons. A deuterium atom (D) is a hydrogen atom with one neutron. As referred to herein, a ratio of deuterium:protium in a compound greater than 1:99 is considered to be greater than that found naturally in hydrogen. The ratio may refer either to active compound(s) comprised in the solid dosage form, or to one or more specified positions in N,N-dimethyltryptamine compound(s) comprised in the solid dosage form, for example the alpha position.

The term N,N-dimethyltryptamine compounds means N,N-dimethyltryptamine and its deuterated analogues. Examples of deuterated analogues are the compounds of Formula I described herein. These deuterated analogues include compounds 1-5 depicted above, including deuterated α,α-diprotio-N,N-dimethyltryptamine compounds such as compound 5. Preferred deuterated analogues are α,α-dideutero-N,N-dimethyltryptamine compounds and α-protio, α-deutero-N,N-dimethyltryptamine compounds.

The term α,α-dideutero-N,N-dimethyltryptamine compounds refers to N,N-dimethyltryptamine compounds with both hydrogen atoms at the α position substituted with deuterium atoms. The term α-protio, α-deutero-N,N-dimethyltryptamine compounds refers to N,N-dimethyltryptamine compounds in which one of the two hydrogen atoms at the α position is substituted with a deuterium atom.

N,N-dimethyltryptamine compounds freely form addition salts with anionic counterions. Throughout the specification, unless a context expressly dictates otherwise, an N,N-dimethyltryptamine compound (in particular N,N-dimethyltryptamine, α,α-dideutero-N,N-dimethyltryptamine compounds and α-protio, α-deutero-N,N-dimethyltryptamine compounds) refers equally to any pharmaceutically acceptable salt, e.g. the fumarate salt.

Typically, acidic reagents may be used to prepare salts, in particular pharmaceutically acceptable salts, of N,N-dimethyltryptamine compounds. Examples of suitable acidic reagents are selected from the group consisting of fumaric acid, hydrochloric acid, tartaric acid, citric acid, hydrobromic acid, sulfuric acid, phosphoric acid, acetic acid, maleic acid, lactic acid, tartaric acid and gluconic acid. Often, where in the form of salts, N,N-dimethyltryptamine compounds, in particular in the solid dosage forms of the invention or otherwise used according to the various aspects of the present invention, and embodiments thereof, are fumarate, hydrochloride, tartrate or citrate salts, in particular fumarate salts.

The compound or compounds present in the solid dosage form of the first aspect of the invention, and indeed those of the second and third (and other, as appropriate) aspects of the invention, may thus be present as N,N-dimethyltryptamine compounds, in particular N,N-dimethyltryptamine, α-protio, α-deutero-N,N-dimethyltryptamine compounds or α,α-dideutero-N,N-dimethyltryptamine compounds as defined herein, in free base or salt form (such as the salts described herein), optionally as solvates (e.g. hydrates) thereof.

According to particular embodiments of the invention, α,α-dideutero-N,N-dimethyltryptamine compounds comprise 0, 1 or 2 deuterium atoms at the 13 position but, other than the presence of 2, 3 or 4 deuterium atoms, are identical to the compound N,N-dimethyltryptamine. According to these particular and other particular embodiments of the invention, α-protio, α-deutero-N,N-dimethyltryptamine compounds may also comprise 0, 1 or 2 deuterium atoms at the 13 position (that is the exocyclic carbon atom directly attached to the five-membered ring in N,N-dimethyltryptamine compounds) but, other than the presence of 1, 2 or 3 deuterium atoms, are identical to the compound N,N-dimethyltryptamine. In preferred embodiments of the first aspect, the solid dosage form comprises 2% or more by weight of one or more α,α-dideutero-N,N-dimethyltryptamine or α-protio, α-deutero-N,N-dimethyltryptamine compounds. In preferred embodiments of the first aspect, the solid dosage form comprises 5% or more by weight of the one or more α,α-dideutero-N,N-dimethyltryptamine or α-protio, α-deutero-N,N-dimethyltryptamine compounds. In preferred embodiments of the first aspect, the solid dosage form comprises 10% or more by weight of the one or more α,α-dideutero-N,N-dimethyltryptamine or α-protio, α-deutero-N,N-dimethyltryptamine compounds. In preferred embodiments of the first aspect, the solid dosage form comprises 15% or more by weight of the one or more α,α-dideutero-N,N-dimethyltryptamine or α-protio, α-deutero-N,N-dimethyltryptamine compounds. In preferred embodiments of the first aspect, the solid dosage form comprises 20% or more by weight of the one or more α,α-dideutero-N,N-dimethyltryptamine or α-protio, α-deutero-N,N-dimethyltryptamine compounds. In preferred embodiments of the first aspect, the solid dosage form comprises 25% or more by weight of the one or more α,α-dideutero-N,N-dimethyltryptamine or α-protio, α-deutero-N,N-dimethyltryptamine compounds. In preferred embodiments of the first aspect, the solid dosage form comprises 30% or more by weight of the one or more α,α-dideutero-N,N-dimethyltryptamine or α-protio, α-deutero-N,N-dimethyltryptamine compounds. In preferred embodiments of the first aspect, the solid dosage form comprises 50% or more by weight of the one or more α,α-dideutero-N,N-dimethyltryptamine or α-protio, α-deutero-N,N-dimethyltryptamine compounds. In preferred embodiments of the first aspect, the solid dosage form comprises 60% or more by weight of the one or more α,α-dideutero-N,N-dimethyltryptamine or α-protio, α-deutero-N,N-dimethyltryptamine compounds. In preferred embodiments of the first aspect, the solid dosage form comprises 75% or more by weight of the one or more α,α-dideutero-N,N-dimethyltryptamine or α-protio, α-deutero-N,N-dimethyltryptamine compounds. In preferred embodiments of the first aspect, the solid dosage form comprises up to 90% by weight of the one or more α,α-dideutero-N,N-dimethyltryptamine or α-protio, α-deutero-N,N-dimethyltryptamine compounds. In preferred embodiments of the first aspect, the solid dosage form comprises up to 95% by weight of the one or more α,α-dideutero-N,N-dimethyltryptamine or α-protio, α-deutero-N,N-dimethyltryptamine compounds. In preferred embodiments of the first aspect, the solid dosage form comprises up to 96% by weight of the one or more α,α-dideutero-N,N-dimethyltryptamine or α-protio, α-deutero-N,N-dimethyltryptamine compounds. In preferred embodiments of the first aspect, the solid dosage form comprises up to 97% by weight of the one or more α,α-dideutero-N,N-dimethyltryptamine or α-protio, α-deutero-N,N-dimethyltryptamine compounds. In preferred embodiments of the first aspect, the solid dosage form comprises up to 98% by weight of the one or more α,α-dideutero-N,N-dimethyltryptamine or α-protio, α-deutero-N,N-dimethyltryptamine compounds.

Accordingly, it will be understood from the foregoing that, according to particular embodiments of the first aspect of the invention, in particular those embodiments discussed in the following five paragraphs, the solid dosage form comprises between 2% and 90%, 2% and 95%, 2% and 96%, 2% and 97%, 2% and 98%, for example between 5% and 90%, 5% and 95%, 5% and 96%, 5% and 97%, 5% and 98%; 10% and 90%, 10% and 95%, 10% and 96%, 10% and 97%, 10% and 98%; 15% and 90%, 15% and 95%, 15% and 96%, 15% and 97%, 15% and 98%; 20% and 90%, 20% and 95%, 20% and 96%, 20% and 97%, 20% and 98%; 25% and 90%, 25% and 95%, 25% and 96%, 25% and 97%, 25% and 98%; 30% and 90%, 30% and 95%, 30% and 96%, 30% and 97%, 30% and 98%; 50% and 90%, 50% and 95%, 50% and 96%, 50% and 97%, 50% and 98%; 60% and 90%, 60% and 95%, 60% and 96%, 60% and 97%, 60% and 98%; or 75% and 90%, 75% and 95%, 75% and 96%, 75% and 97%, 75% and 98%, by weight of the one or more α,α-dideutero-N,N-dimethyltryptamine or α-protio, α-deutero-N,N-dimethyltryptamine compounds.

In embodiments of the first aspect, the solid dosage form comprises a combination of N,N-dimethyltryptamine and one or more α,α-dideutero-N,N-dimethyltryptamine compounds, for example a combination of N,N-dimethyltryptamine and α,α-dideutero-N,N-dimethyltryptamine or a combination of N,N-dimethyltryptamine, α-protio, α-deutero-N,N-dimethyltryptamine and α,α-dideutero-N,N-dimethyltryptamine.

In preferred embodiments of the first aspect, the solid dosage form comprises a combination of N,N-dimethyltryptamine and 2% or more by weight of α,α-dideutero-N,N-dimethyltryptamine.

In preferred embodiments of the first aspect, the solid dosage form comprises 2% or more by weight of α,α-dideutero-N,N-dimethyltryptamine.

It will be understood that, wherever a solid dosage form comprises 2% or more by weight of one or more α,α-dideutero-N,N-dimethyltryptamine compounds, that such solid dosage forms may comprise up to 95% by weight of one or more α,α-dideutero-N,N-dimethyltryptamine compounds, or up to 96% by weight, up to 97% by weight or up to 98% by weight.

In preferred embodiments of the first aspect, the solid dosage form comprises or further comprises, for example further comprises, α-protio, α-deutero-N,N-dimethyltryptamine or a pharmaceutically acceptable salt thereof.

According to other preferred embodiments of the first aspect of the invention, the solid dosage form comprises up to 50% by weight, based on the total weight of the solid dosage form, of one or more compounds selected from α,α-dideutero-N,N-dimethyltryptamine compounds, α-protio, α-deutero-N,N-dimethyltryptamine compounds and pharmaceutically acceptable salts thereof. It will be understood that, in such embodiments, such compositions may comprise 2% or more by weight, for example 5% or more, 10% more, 15% more, 20% or more, 25% or more or 30% or more, based on the total composition, of the said one or more compounds.

In embodiments of the invention, the two or more N,N-dimethyltryptamine compounds constitute up to 50% by weight of the total solid dosage form. When the solid dosage forms of the present invention are solid oral dosage forms, what has been a persistent challenge—to deliver a sufficiently high dose of an N,N-dimethyltryptamine compound of the present invention to expose the patient to sufficient in vivo DMT concentrations to elicit a psychedelic experience—can be overcome: such solid oral dosage forms can elicit a psychedelic experience without coadministration with inhibitors of metobolising enzymes such as MAOs.

According to other preferred embodiments of the first aspect of the invention, the solid dosage form comprises greater than 50% by weight and up to 95% by weight, based on the total weight of the solid dosage form, of one or more compounds selected from α,α-dideutero-N,N-dimethyltryptamine compounds, α-protio, α-deutero-N,N-dimethyltryptamine compounds and pharmaceutically acceptable salts thereof. It will be understood that, in such embodiments, such solid dosage forms may comprise 2% or more by weight, for example 5% or more, 10% more, 15% more, 20% or more, 25% or more or 30% or more, based on the total solid dosage form, of the said one or more compounds. Preferably solid oral dosage forms of the present invention comprise 25% or more by weight of an N,N-dimethyltryptamine compound.

Typically, the composition and solid dosage forms of the invention comprise N,N-dimethyltryptamine. However, certain embodiments of the first aspect of the present invention are devoid of N,N-dimethyltryptamine. In certain embodiments, the two or more N,N-dimethyltryptamine compounds comprises exclusively deuterated N,N-dimethyltryptamine compounds. Such embodiments are preferred for use in solid oral dosage forms for eliciting a breakthrough psychedelic experience in a patient.

According to specific embodiments, the solid dosage forms of the present invention, including all of the embodiments described herein, including but not limited to those embodiments comprising N,N-dimethyltryptamine, consist essentially of two or more N,N-dimethyltryptamine compounds (i.e. compounds selected from N,N-dimethyltryptamine and its deuterated analogues, in particular those deuterated at the alpha and optionally beta positions) or pharmaceutically acceptable salts of these. By the solid dosage form consisting essentially of two or more N,N-dimethyltryptamine compounds is meant that the solid dosage form may comprise additional components (other than N,N-dimethyltryptamine compounds) but that the presence of these additional components will not materially affect the essential characteristics of the solid dosage form. In particular, solid dosage forms consisting essentially of N,N-dimethyltryptamine compounds will not comprise material amounts of other pharmaceutically active substances (i.e. material amounts of other drug substances).

Even more typically, the solid dosage forms of the present invention, including all of the embodiments described herein, including but not limited to those embodiments comprising N,N-dimethyltryptamine, consist of two or more N,N-dimethyltryptamine compounds.

The solid dosage form of the present invention may comprise from 2% to 98% by weight of N,N-dimethyltryptamine, and preferably comprises from 5% to 95% by weight of N,N-dimethyltryptamine. Preferred solid dosage forms of the present invention comprise from 10% to 90% by weight of N,N-dimethyltryptamine, or from 15% to 85% by weight of N,N-dimethyltryptamine, or from 20% to 80% by weight of N,N-dimethyltryptamine, or from 25% to 75% by weight of N,N-dimethyltryptamine, or from 30% to 70% by weight of N,N-dimethyltryptamine, or from 40% to 60% by weight of N,N-dimethyltryptamine.

The solid dosage form of the present invention preferably comprises from 5% to 95% by weight of a N,N-dimethyltryptamine compound selected from α,α-dideutero-N,N-dimethyltryptamine and α,α,β,β-tetradeutero-N,N-dimethyltryptamine.

According to particular embodiments, the invention provides a solid dosage form comprising one or more compounds (for example one compound) of Formula I:

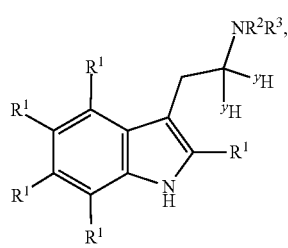
(I)

wherein the ratio of deuterium:protium in the compound is greater than that found naturally in hydrogen:

each $R^1$ is independently selected from H and D;

$R^2$ is selected from $CH_3$ and $CD_3$;

$R^3$ is selected from $CH_3$ and $CD_3$;

each $^yH$ is independently selected from H and D, or a pharmaceutically acceptable salt thereof.

In preferred embodiments, each $R^1$ is H. In primary embodiments, both $^yH$ are D. In secondary embodiments, both $R^2$ and $R^3$ are $CD_3$.

Particularly preferred solid dosage forms according to the second aspect of the present invention comprise one or more compound selected from Compounds 1 to 5 (supra), or a pharmaceutically acceptable salt thereof.

The skilled person is able to readily access compounds of Formula I within his or her normal ability. For example, Mannich reactions between the acidic terminal proton of the terminal propynes shown below, amines of formula $NR^2R^3$ and optionally deuterated formaldehyde of formula $C(^yH)_2O$, followed by reduction of the carbon-carbon triple bond in the resultant product, affords the gem-diethoxy compounds depicted:

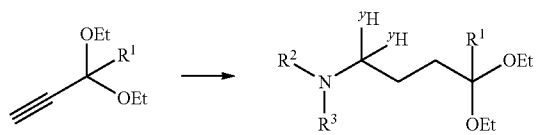

In this scheme, $R^1$ may be protium or deuterium, and corresponds (see infra) to the $R^1$ depicted in the five-membered ring of Formula I. The gem-diethoxy compounds may be reacted, in a Fischer indole synthesis (for example involving heating in the presence of dilute (e.g. 4%) sulfuric acid for about two hours (other conditions may be readily envisaged by a skilled person)), with an optionally deuterated phenyl hydrazine to form the desired compound of Formula I as depicted below:

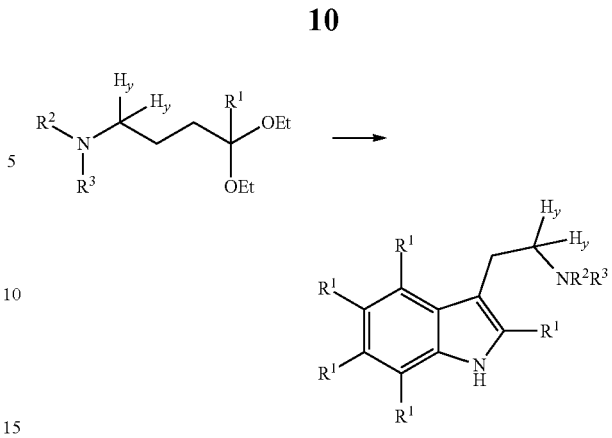

According to a seventh aspect of the invention, there is provided a pharmaceutical composition suitable for oral administration comprising a solid dosage form as described herein, for example in accordance with the first aspect of the invention, in combination with a pharmaceutically acceptable excipient.

The pharmaceutical composition of the seventh aspect of the invention comprises a solid oral dosage form as described herein, for example in accordance with the first aspect of the invention, in combination with one or more pharmaceutically acceptable excipients. Suitable pharmaceutical solid oral dosage forms (and other solid dosage forms of the invention) can be prepared by the skilled person, with examples of pharmaceutically acceptable excipients including but not being limited to those described in Gennaro et. al., Remington: *The Science and Practice of Pharmacy*, $20^{th}$ Edition, Lippincott, Williams and Wilkins, 2000 (specifically part 5: pharmaceutical manufacturing). Suitable excipients are also described in the Handbook of Pharmaceutical Excipients, $2^{nd}$ Edition; Editors A. Wade and P. J. Weller, American Pharmaceutical Association, Washington, The Pharmaceutical Press, London, 1994.

The solid dosage forms of the invention are pharmaceutical compositions, which may be compressed into solid dosage units, such as tablets, or be processed into capsules or suppositories. According to particular embodiments, therefore, the solid dosage form may be in the form of such a solid dosage unit, for example a tablet capsule or suppository. For making dosage units, including tablets, the use of conventional additives such as fillers, colorants, polymeric binders and the like is contemplated. In general, any pharmaceutically acceptable additive can be used.

Suitable fillers with which the pharmaceutical solid dosage forms can be prepared and administered include lactose, starch, cellulose and derivatives thereof, and the like, or mixtures thereof used in suitable amounts. The solid dosage forms described herein may be of use in parenteral (e.g. mucosal) administration. For parenteral administration, aqueous suspensions, isotonic saline solutions and sterile injectable solutions may be used, containing pharmaceutically acceptable dispersing agents and/or wetting agents, such as propylene glycol or butylene glycol.

In preferred embodiments of the seventh aspect, the solid oral dosage form is selected from a tablet, which may be coated, or may alternatively be an orally dispersing tablet, a capsule, a dry powder, for example an inhalable dry powder, a patch, for example a buccal patch, and a film. As used herein, the term 'solid oral dosage form' refers to any solid dosage form suitable for administration via the oral cavity. In embodiments of the invention in which the solid dosage form is not a solid oral dosage form, the solid dosage form may be selected from a powder, for example a powder for injection, a patch, for example a transdermal patch, and a tablet, for example a suppository.

The invention also provides a pharmaceutical solid dosage form of the invention, in combination with packaging material suitable for the solid dosage form, the packaging material including instructions for the use of the pharmaceutical solid dosage form.

The solid dosage forms of the invention are useful in therapy and may be administered to a patient in need thereof. As used herein, the term 'patient' preferably refers to a human patient, but may also refer to a domestic mammal. The term does not encompass laboratory mammals.

In accordance with the third aspect of the invention, there is provided a solid dosage form of the invention, for example as defined according to its first aspect, for use in a method of treating a psychiatric or neurological disorder in a patient. The fourth aspect of the invention provides a method of treating a psychiatric or neurological disorder comprising administering to a patient in need thereof a solid dosage form of the invention, for example as defined according the first aspect; and the fifth aspect provides the use of a solid dosage form of the invention, for example as defined according to its first aspect, in the manufacture of a medicament for use in a method of treating a psychiatric or neurological disorder in a patient. The invention is also of use in methods of treating psychocognitive disorders in patients.

As used herein the term 'psychiatric disorder' is a clinically significant behavioural or psychological syndrome or pattern that occurs in an individual and that is associated with present distress (e.g., a painful symptom) or disability (i.e., impairment in one or more important areas of functioning) or with a significantly increased risk of suffering death, pain, disability, or an important loss of freedom. The term psychiatric disorder encompasses psychiatric disorders which may be associated with one or more cognitive impairment.

Diagnostic criteria for psychiatric and neurological, and psychocognitive, disorders referred to herein are provided in the Diagnostic and Statistical Manual of Mental Disorders, Fifth Edition, (DSM-5), the contents of which are incorporated herein by reference.

As used herein the term 'obsessive-compulsive disorder' is defined by the presence of either obsessions or compulsions, but commonly both. The symptoms can cause significant functional impairment and/or distress. An obsession is defined as an unwanted intrusive thought, image or urge that repeatedly enters the person's mind. Compulsions are repetitive behaviours or mental acts that the person feels driven to perform. Typically obsessive-compulsive disorder (OCD) manifests as one or more obsession which drives adoption of a compulsion. For example, an obsession with germs may drive a compulsion to clean. A compulsion can either be overt and observable by others, such as checking that a door is locked, or a covert mental act that cannot be observed, such as repeating a certain phrase in one's mind.

As used herein the term 'depressive disorder' includes major depressive disorder, persistent depressive disorder, bipolar disorder, bipolar depression, and depression in terminally ill patients.

As used herein the term 'major depressive disorder' (MDD, also referred to as major depression or clinical depression) is defined as the presence of five or more of the following symptoms over a period of two-weeks or more (also referred to herein as a 'major depressive episode'), most of the day, nearly every day:

depressed mood, such as feeling sad, empty or tearful (in children and teens, depressed mood can appear as constant irritability);
significantly reduced interest or feeling no pleasure in all or most activities;
significant weight loss when not dieting, weight gain, or decrease or increase in appetite (in children, failure to gain weight as expected);
insomnia or increased desire to sleep;
either restlessness or slowed behaviour that can be observed by others;
fatigue or loss of energy;
feelings of worthlessness, or excessive or inappropriate guilt;
trouble making decisions, or trouble thinking or concentrating;
recurrent thoughts of death or suicide, or a suicide attempt.

At least one of the symptoms must be either a depressed mood or a loss of interest or pleasure.

Persistent depressive disorder, also known as dysthymia, is defined as a patient exhibiting the following two features:
A. has depressed mood for most the time almost every day for at least two years. Children and adolescents may have irritable mood, and the time frame is at least one year.
B. While depressed, a person experiences at least two of the following symptoms:
  Either overeating or lack of appetite.
  Sleeping too much or having difficulty sleeping.
  Fatigue, lack of energy.
  Poor self-esteem.
  Difficulty with concentration or decision making.

As used herein the term 'treatment resistant depression' describes MDD which fails to achieve an adequate response to an adequate treatment with standard of care therapy.

As used herein 'bipolar disorder' also known as manic-depressive illness, is a disorder that causes unusual shifts in mood, energy, activity levels, and the ability to carry out day-to-day tasks.

There are two defined sub-categories of bipolar disorder; all of them involve clear changes in mood, energy, and activity levels. These moods range from periods of extremely "up," elated, and energised behaviour (known as manic episodes, and defined further below) to very sad, "down," or hopeless periods (known as depressive episodes). Less severe manic periods are known as hypomanic episodes.

Bipolar I Disorder—defined by manic episodes that last at least 7 days, or by manic symptoms that are so severe that the person needs immediate hospital care. Usually, depressive episodes occur as well, typically lasting at least 2 weeks. Episodes of depression with mixed features (having depression and manic symptoms at the same time) are also possible.

Bipolar II Disorder—defined by a pattern of depressive episodes and hypomanic episodes, but not the full-blown manic episodes described above.

As used herein 'bipolar depression' is defined as an individual who is experiencing depressive symptoms with a previous or coexisting episode of manic symptoms, but does not fit the clinical criteria for bipolar disorder.

As used herein the term 'anxiety disorder' includes generalised anxiety disorder, phobia, panic disorder, social anxiety disorder, and post-traumatic stress disorder.

'Generalised anxiety disorder' (GAD) as used herein means a chronic disorder characterised by long-lasting anxiety that is not focused on any one object or situation. Those suffering from GAD experience non-specific persistent fear and worry, and become overly concerned with everyday matters. GAD is characterised by chronic excessive worry accompanied by three or more of the following symptoms: restlessness, fatigue, concentration problems, irritability, muscle tension, and sleep disturbance.

'Phobia' is defined as a persistent fear of an object or situation the affected person will go to great lengths to avoid, typically disproportional to the actual danger posed. If the feared object or situation cannot be avoided entirely, the affected person will endure it with marked distress and significant interference in social or occupational activities.

A patient suffering a from a 'panic disorder' is defined as one who experiences one or more brief attack (also referred to as a panic attack) of intense terror and apprehension, often marked by trembling, shaking, confusion, dizziness, nausea, and/or difficulty breathing. A panic attack is defined as a fear or discomfort that abruptly arises and peaks in less than ten minutes.

'Social anxiety disorder' is defined as an intense fear and avoidance of negative public scrutiny, public embarrassment, humiliation, or social interaction. Social anxiety often manifests specific physical symptoms, including blushing, sweating, and difficulty speaking.

'Post-traumatic stress disorder' (PTSD) is an anxiety disorder that results from a traumatic experience. Post-traumatic stress can result from an extreme situation, such as combat, natural disaster, rape, hostage situations, child abuse, bullying, or even a serious accident. Common symptoms include hypervigilance, flashbacks, avoidant behaviours, anxiety, anger and depression.

As used herein the term 'substance abuse' means a patterned use of a drug in which the user consumes the substance in amounts or with methods which are harmful to themselves or others.

As used herein the term 'an avolition disorder' refers to a disorder which includes as a symptom the decrease in motivation to initiate and perform self-directed purposeful activities.

As used herein the term 'brain injury disorder' refers to an injury to the brain that occurs after birth and is not congenital, degenerative or hereditary. The term encompasses traumatic brain injury, for example from a car accident or a sports injury, and acquired brain injury, such as ischaemic stroke, transient ischaemic stroke, haemorrhagic stroke, brain tumour, meningitis or encephalitis.

In preferred embodiments of the present invention, the psychiatric or neurological disorder is selected from (i) an obsessive compulsive disorder, (ii) a depressive disorder, (iii) a schizophrenia disorder, (iv) a schizotypal disorder, (v) an anxiety disorder, (vi) substance abuse, (vii) an avolition disorder, and (viii) a brain injury disorder.

In certain embodiments of the present invention, the psychiatric or neurological disorder is selected from (i) an obsessive compulsive disorder, (ii) a depressive disorder, (iii) an anxiety disorder, (iv) substance abuse, and (v) an avolition disorder.

According to particular embodiments of the third to fifth aspects of the present invention, the depressive disorder is major depressive disorder. According to still more particular embodiments, the major depressive disorder is treatment-resistant major depressive disorder.

Solid dosage forms comprising N,N-dimethyltryptamine compounds of the present invention can be synthesised following the reaction schemes (synthetic schemes) provided in Scheme 1 and Scheme 2 below. The chemistry depicted in the schemes was reported by P E Morris and C Chiao (*Journal of Labelled Compounds And Radiopharmaceuticals*, Vol. XXXIII, No. 6, 455-465 (1993)). Solid dosage forms comprising N,N-dimethyltryptamine compounds of the present invention can also be synthesised following the synthetic scheme depicted in Scheme 3 in Example 4 below.

It will be immediately understood that access to deuterated N,N-dimethyltryptamine compounds in which the one or both of the methyl groups of the dimethyl moiety are substituted with $CD_3$ groups may be achieved through the use of appropriate deuterated dimethylamines (instead of dimethylamine as depicted in Schemes 1 to 3), which are commercially available, for example commercially available $d_7$-dimethylamine (i.e. $DN(CD_3)_2$) and $d_6$-dimethylamine (i.e. di(trideuteromethyl)amine).

The relative proportions of N,N-dimethyltryptamine against α-protio, α-deutero-N,N-dimethyltryptamine compounds and/or α,α-dideutero-N,N-dimethyltryptamine compounds, may be controlled by varying the ratio of lithium aluminium hydride and lithium aluminium deuteride in the reducing agent. In the same way, the relative proportions of deuterated, but α,α-diprotio-N,N-dimethyltryptamine compounds against α-protio, α-deutero-N,N-dimethyltryptamine compounds and/or α,α-dideutero-N,N-dimethyltryptamine compounds, may be controlled by varying the ratio of lithium aluminium hydride and lithium aluminium deuteride in the reducing agent.

Relative proportions may further be varied by adding one or more of N,N-dimethyltryptamine or α,α-dideutero-N,N-dimethyltryptamine to the solid dosage forms described hereinabove.

A particular advantage of solid dosage forms prepared by the synthetic method described in Scheme 3 is that the reductions described in accordance this method allow particularly high purities to be obtained, without the necessity for subsequent chromatographic purification (e.g. column chromatography), thereby increasing the efficiency through which solid dosage forms of the invention may be prepared. Moreover, the ability to avoid the use of chromatography in order to achieve high purities makes scale up more efficient and therefore cost-effective.

Identification of the solid dosage forms resultant from the reduction step in methods described herein may be achieved, if desired, by chromatographic separation of the components of the mixtures by conventional means at the disposal of the skilled person in combination with spectroscopic and/or mass spectrometric analysis.

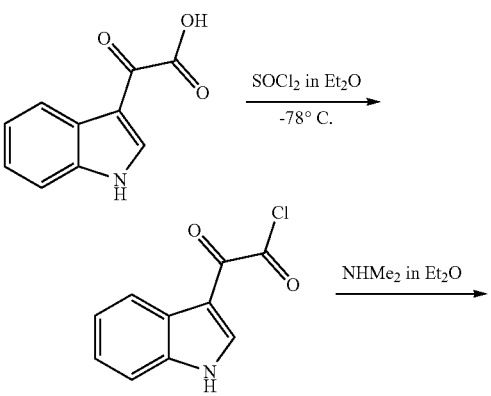

Scheme 1

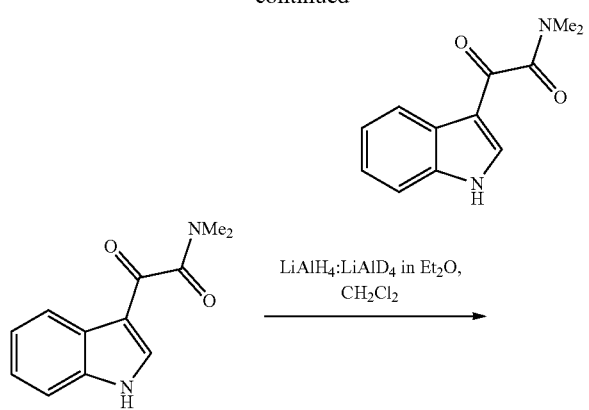

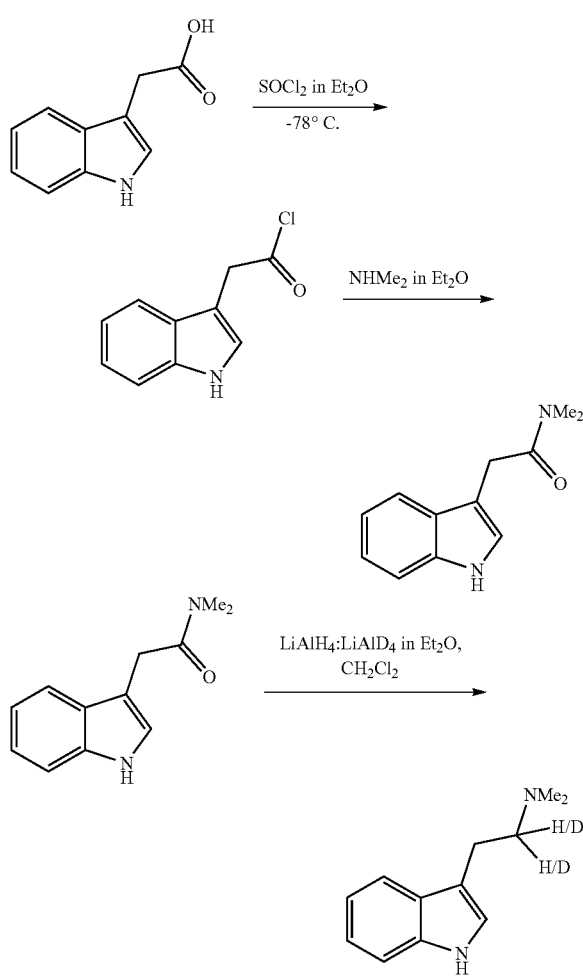

Scheme 2

Alternative solid dosage forms of the present invention are obtainable by mixing N,N-dimethyltryptamine, obtainable by Scheme 1 or Scheme 2 when the reducing agent is exclusively lithium aluminium hydride, with an α,α-dideutero-N,N-dimethyltryptamine compound obtainable from Scheme 1 or Scheme 2 when the reducing agent is exclusively lithium aluminium deuteride.

The solid dosage forms described hereinabove may be further modified by adding one or more N,N-dimethyltryptamine compounds, for example one or more α,α-dideutero-N,N-dimethyltryptamine or α-protio, α-deutero-N,N-dimethyltryptamine compounds. Stocks of such N,N-dimethyltryptamine compounds may be obtained, for example, from the chromatographic separation described above. In this way, for example, the isolated compounds of the invention may be obtained.

Whilst identification of the compositions of the solid dosage forms resultant from the reduction described herein may be achieved by chromatographic separation of the components of the mixtures, in combination with spectroscopic and/or mass spectrometric analysis, a particular benefit of the present invention is that, according to particular embodiments, there may be no necessity to do so. This is because, over and above the purities achievable in accordance with the present invention, we have as alluded to above recognised that there is a quantifiable relationship between the extent of deuteration (or in other words the quantity or proportion of deuterium in the N,N-dimethyltryptamine compounds in the solid dosage forms of the present invention) and the metabolic half-life of the resultant solid dosage form. The extent of deuteration may be controlled through the amount of deuterium-containing reducing agent used in the method of the invention, through which (according to particular embodiments) the solid dosage forms of the invention may be obtained, and thus control exercised, in a predictable way, over potentiation of the metabolic half-life of the parent compound (undeuterated N,N-dimethyltryptamine).

Figure 2:
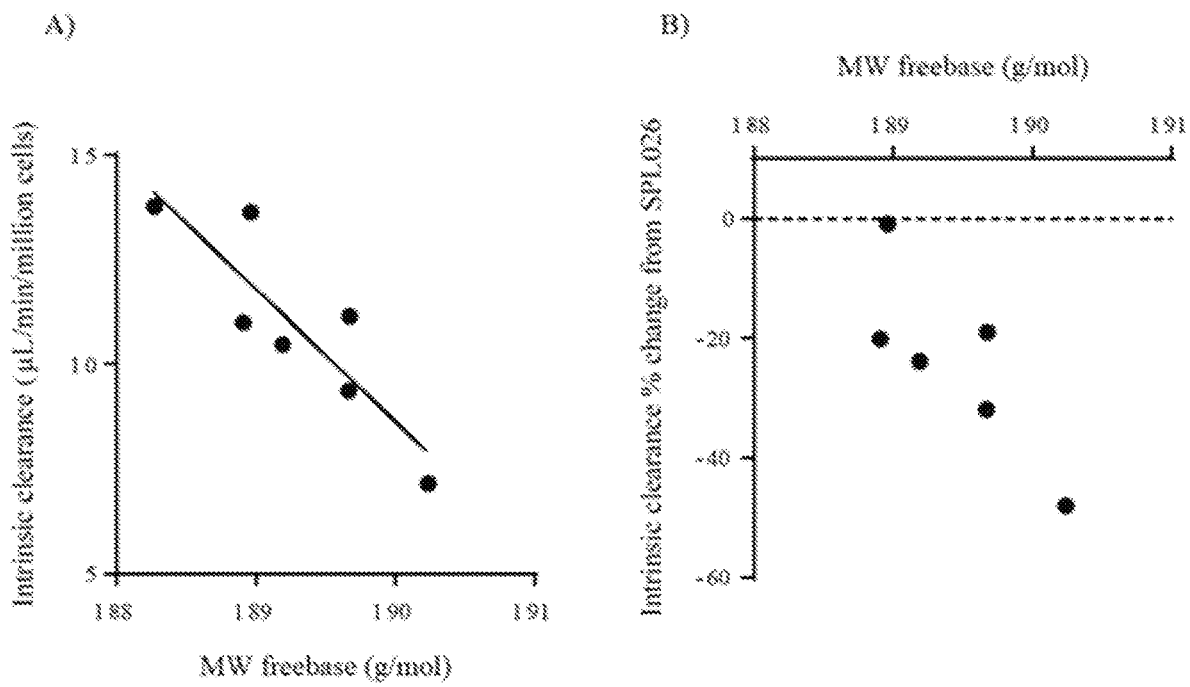
FIG. 2 shows In vitro intrinsic clearance for DMT and 6 deuterium-containing compositions described in Example 4. A) Linear regression analysis. The $r^2$ value for intrinsic clearance is 0.7648; where the slope was found to be significantly different to zero, p=0.01. B) Intrinsic clearance of deuterated analogues as a percent change from (undeuterated) DMT fumarate (dashed line).

In particular, as detailed in Example 4 and related FIGS. 1 and 2, we have demonstrated that increasing deuterium enrichment at the α-carbon of N,N-dimethyltryptamine increases metabolic stability, leading to a decrease in clearance and longer half-life. A linear relationship exists between molecular weight and half-life.

Such types of solid dosage form constitute specific embodiments of the first aspect of the invention. According to these specific embodiments, the solid dosage form consists essentially of a mixture of N,N-dimethyltryptamine and one or both of α-protio, α-deutero-N,N-dimethyltryptamine and α,α-dideutero-N,N-dimethyltryptamine, the solid dosage form optionally being in the form of a pharmaceutically acceptable salt, wherein the mean molecular weight of N,N-dimethyltryptamine compounds (N,N-dimethyltryptamine, α-protio, α-deutero-N,N-dimethyltryptamine and α,α-dideutero-N,N-dimethyltryptamine) present in the solid dosage form is greater than 188.28 grams per mole. According to alternative specific embodiments, the solid dosage form consists essentially of a mixture of N,N-dimethyltryptamine and one or both of α-protio, α-deutero-N,N-dimethyltryptamine and α,α-dideutero-N,N-dimethyltryptamine, the solid dosage form optionally being in the form of a pharmaceutically acceptable salt, wherein the mean molecular weight of N,N-dimethyltryptamine compounds present in the solid dosage form is less than or equal to 190.28. According to still more specific embodiments, the composition consists essentially of a mixture of N,N-dimethyltryptamine and one or both of α-protio, α-deutero-N,N- dimethyltryptamine and α,α-dideutero-N,N-dimethyltryptamine, the composition optionally being in the form of a pharmaceutically acceptable salt, wherein the mean molecular weight of N,N-dimethyltryptamine, α-protio, α-deutero-N,N-dimethyltryptamine and α,α-dideutero-N,N-dimethyltryptamine present in the composition is from 188.28 to 190.28.

More generally, with respect to solid dosage forms that may comprise other N,N-dimethyltryptamine compounds, in particular other N,N-dimethyltryptamine compounds with more extensive deuteration, the mean molecular weight of N,N-dimethyltryptamine compounds in such solid dosage forms may be greater than 188.28 grams per mole up to a maximum molecular weight of 204.37 grams per mole, excluding the weight of any counterion in a pharmaceutically acceptable salt (see the next paragraph). The mean molecular weight of N,N-dimethyltryptamine compounds in these particular solid dosage forms is from 188.28 to 196.32. In such solid dosage forms, therefore, it will be understood that these may consist essentially of a mixture of N,N-dimethyltryptamine compounds (for example N,N-dimethyltryptamine and one or more deuterated analogues, for example one or more compounds of Formula I, for example compounds 1-5).

As used herein, mean molecular weight means the weighted average of molecular weights of the N,N-dimethyltryptamine and its deuterated analogues comprised in the solid dosage form, for example (in particular embodiments) one or both of α-protio, α-deutero-N,N-dimethyltryptamine and α,α-dideutero-N,N-dimethyltryptamine, as measured by an appropriate mass spectroscopic technique, for example LC-MS SIM (selected-ion monitoring), ignoring any weight contribution by formation of pharmaceutically acceptable salts, where applicable.

It will be understood that providing solid dosage forms with such specific mean molecular weights can be achieved by those skilled in the art through the teachings herein, in particular by adjusting the relative proportions of lithium aluminium hydride and lithium aluminium deuteride in the reductions described herein.

In this context, by reciting that the solid dosage form consists essentially of the mixture of N,N-dimethyltryptamine and one or both of α-protio, α-deutero-N,N-dimethyltryptamine and α,α-dideutero-N,N-dimethyltryptamine means that the solid dosage form may comprise additional components to these but that the presence of such additional components will not materially affect the essential characteristics of the solid dosage form. In particular, the solid dosage form will not comprise material quantities of other pharmaceutically active compounds, including other N,N-dimethyltryptamine compounds. Thus material quantities of other deuterated N,N-dimethyltryptamine compounds, in particular β-deutero-N,N-dimethyltryptamine compounds and β,β-dideutero-N,N-dimethyltryptamine compounds, such as β-deutero-N,N-dimethyltryptamine and β,β-dideutero-N,N-dimethyltryptamine and β-deutero-N,N-dimethyltryptamine compounds and β,β-dideutero-N,N-dimethyltryptamine compounds having respectively one or two deuterium atoms in place of hydrogen atoms at the α position are not present in solid dosage forms of such embodiments.

In other words, and alternatively put, the solid dosage forms according to these specific embodiments constitute a drug substance comprising a biologically active ingredient consisting essentially of a mixture of N,N-dimethyltryptamine and one or more of α-protio, α-deutero-N,N-dimethyltryptamine and α,α-dideutero-N,N-dimethyltryptamine, wherein the biologically active ingredient has a mean molecular weight greater than or equal to 188.28 grams per mole and/or less than or equal to 190.28 grams per mole and wherein the drug substance is optionally in the form of a pharmaceutically acceptable salt.

It will be understood that the solid dosage forms according to embodiments comprise one or more of α-protio, α-deutero-N,N-dimethyltryptamine and α,α-dideutero-N,N-dimethyltryptamine in amounts greater than found in isotopically unenriched N,N-dimethyltryptamine. It will also be understood that the greater the proportion of α-protio, α-deutero-N,N-dimethyltryptamine and α,α-dideutero-N,N-dimethyltryptamine in these specific embodiments, the higher the mean molecular weight of the solid dosage form.

According to more specific embodiments, the mean molecular weight of N,N-dimethyltryptamine compounds present in the solid dosage form is greater than or equal to 188.9 grams per mole.

According to still more specific embodiments of the specific embodiments described herein, including solid dosage forms in which the mean molecular weight of N,N-dimethyltryptamine compounds (for example N, N-dimethyltryptamine, α-protio, α-deutero-N,N-dimethyltryptamine and α,α-dideutero-N,N-dimethyltryptamine) present in the solid dosage form is from 188.9 to 189.7, for example 188.90 to 189.70, the solid dosage form optionally is in the form of a pharmaceutically acceptable salt, by which it will be understood that the N,N-dimethyltryptamine compounds present in the solid dosage form are present in pharmaceutically acceptable salt form. Such salts may be as described elsewhere herein and, according to yet more specific embodiments, the solid dosage form is in the form of a fumarate salt.

Each and every patent and non-patent reference referred to herein is hereby incorporated by reference in its entirety, as if the entire contents of each reference were set forth herein in its entirety.

EXAMPLES

Example 1

2-(3-indolyl)-N,N-dimethylacetamide is synthesised as described in Morris and Chiao (1993), Journal of labelled compounds and radiopharmaceuticals, Vol.)(XXIII, No. 6.

0.063 g $LiAlH_4$ and 0.278 g $LiAlD_4$ (20:80 molar ratio of $LiAlH_4$:$LiAlD_4$) are suspended in 25 ml dry $Et_2O$ with magnetic stirring. 0.785 g of 2-(3-indolyl)-N,N-dimethylacetamide is dissolved in 300 ml and added dropwise to the stirred suspension. The reagents are heated under reflux for 3 hours, then cooled in an ice bath and quenched dropwise with water. The resulting mixture is filtered, dried, and the solvents removed under vacuum, to yield approx. 0.5 g of a composition consisting of 3 molar % N,N-dimethyltryptamine, 28 molar % α-protio, α-deutero-N,N-dimethyltryptamine and 69 molar % of α,α-dideutero-N,N-dimethyltryptamine.

Example 2

0.173 g $LiAlH_4$ and 0.156 g $LiAlD_4$ (55:45 molar ratio of $LiAlH_4$:$LiAlD_4$) are suspended in 25 ml dry $Et_2O$ with magnetic stirring. 0.785 g of 2-(3-indolyl)-N,N-dimethylacetamide is dissolved in 300 ml and added dropwise to the stirred suspension. The reagents are heated under reflux for 3 hours, then cooled in an ice bath and quenched dropwise with water. The resulting mixture is filtered, dried, and the solvents removed under vacuum, to yield approx. 0.5 g of a composition consisting of 24 molar % N,N-dimethyltryptamine, 50 molar % α-protio, α-deutero-N,N-dimethyltryptamine and 26 molar % of α,α-dideutero-N,N-dimethyltryptamine.

Example 3

0.293 g LiAlH$_4$ and 0.035 g LiAlD$_4$ (90:10 molar ratio of LiAlH$_4$:LiAlD$_4$) are suspended in 25 ml dry Et$_2$O with magnetic stirring. 0.785 g of 2-(3-indolyl)-N,N-dimethylacetamide is dissolved in 300 ml and added dropwise to the stirred suspension. The reagents are heated under reflux for 3 hours, then cooled in an ice bath and quenched dropwise with water. The resulting mixture is filtered, dried, and the solvents removed under vacuum, to yield approx. 0.5 g of a composition consisting of 76 molar % N,N-dimethyltryptamine, 22 molar % α-protio, α-deutero-N,N-dimethyltryptamine and 2 molar % of α,α-dideutero-N,N-dimethyltryptamine.

Example 4

Use of Human Hepatocytes to Assess the In Vitro Intrinsic Clearance of Deuterated DMT Analogue Blends Relative to DMT In vitro determination of intrinsic clearance is a valuable model for predicting in vivo hepatic clearance. The liver is the main organ of drug metabolism in the body, containing both phase I and phase II drug metabolising enzymes, which are present in the intact cell.

Synthesis of Samples

N,N-DMT 220.9 g (as free base) was prepared as N,N-DMT fumarate, using the chemistry depicted in Scheme 3. An additional 4-6 g of six partially deuterated mixtures were also produced using modified conditions.

Scheme 3

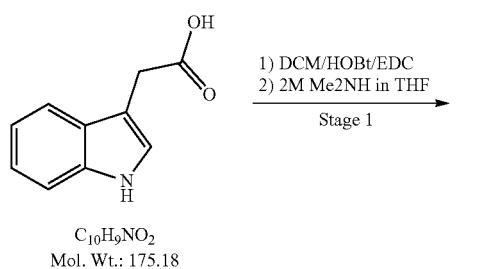

C$_{10}$H$_9$NO$_2$
Mol. Wt.: 175.18

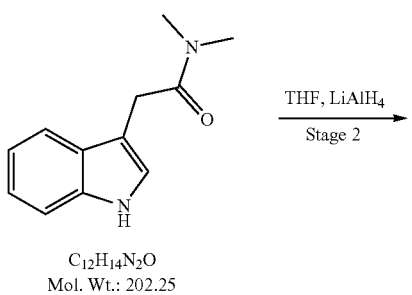

C$_{12}$H$_{14}$N$_2$O
Mol. Wt.: 202.25

-continued

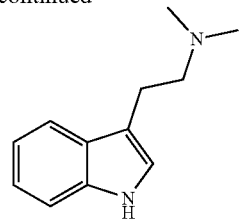

C$_{12}$H$_{16}$N$_2$
Mol. Wt.: 188.27

Stage 3 | EtOH
Fumaric acid

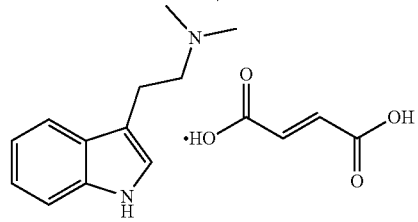

C$_{16}$H$_{20}$N$_2$O$_4$
Mol. Wt.: 304.34

Synthesis of DMT

Stage 1: Coupling of indole-3-acetic acid and dimethylamine

To a 5 L vessel under N$_2$ was charged indole-3-acetic acid (257.0 g, 1.467 mol), hydroxybenzotriazole (HOBt, ~20% wet) (297.3 g, 1.760 mol) and dichloromethane (2313 ml) to give a milky white suspension. 1-Ethyl-3-(3-dimethylaminopropyl) carbodiimide hydrochloride (EDC·HCl, 337.5 g, 1.760 mol) was then charged portion-wise over 5 minutes at 16-22° C. The reaction mixture was stirred for 2 hours at ambient temperature before 2M dimethylamine in THF (1100 ml, 2.200 mol) was charged dropwise over 20 minutes at 20-30° C. The resultant solution was stirred at ambient temperature for 1 hour where HPLC indicated 1.1% indole-3-acetic acid and 98.1% target product referred to as Stage 1). The reaction mixture was then charged with 10% K$_2$CO$_3$ (1285 ml) and stirred for 5 minutes. The layers were separated, and the upper aqueous layer extracted with dichloromethane (643 ml×2). The organic extracts were combined and washed with saturated brine (643 ml). The organic extracts were then dried over MgSO$_4$, filtered and concentrated in vacuo at 45° C. This provided 303.1 g of crude Stage 1 as an off-white sticky solid. The crude material was then subjected to a slurry in tert-butyl methyl ether (TBME, 2570 ml) at 50° C. for 2 hours before being cooled to ambient temperature, filtered and washed with TBME (514 ml×2). The filter-cake was then dried in vacuo at 50° C. to afford Stage 1 266.2 g (yield=90%) as an off-white solid in a purity of 98.5% by HPLC and >95% by NMR.

Stage 2: Preparation of DMT

To a 5 L vessel under N$_2$ was charged Stage 1 (272.5 g, 1.347 mol) and tetrahydrofuran (THF, 1363 ml) to give an off-white suspension. 2.4 M LiAlH$_4$ in THF (505.3 ml, 1.213 mol) was then charged dropwise over 35 minutes at 20-56° C. to give an amber solution. The solution was heated to 60° C. for 2 hours where HPLC indicated Stage 1 ND, target product bracket referred to as Stage 2, 92.5%), Impurity 1

(2.6%), Impurity 2 (1.9%). The complete reaction mixture was cooled to ambient temperature and then charged to a solution of 25% Rochelle's salts (aq) (2725 ml) dropwise over 30 minutes at 20-30° C. The resultant milky white suspension was allowed to stir at 20-25° C. for 1 hour after which the layers were separated and the upper organic layer washed with saturated brine (681 ml). The organic layer was then dried over $MgSO_4$, filtered and concentrated in vacuo at 45° C. The resultant crude oil was subjected to an azeotrope from ethanol (545 ml×2). This provided 234.6 g (yield=92%) of Stage 2 in a purity of 95.0% by HPLC and >95% by NMR.

Stage 3a (i)-(iii): Preparation of Seed Crystals of DMT Fumarate (i) Stage 2 (100 mg) was taken up in 8 volumes of isopropyl acetate and warmed to 50° C. before charging fumaric acid (1 equivalent) as a solution in ethanol. The flask was then allowed to mature at 50° C. for 1 hour before cooling to room temperature and stirring overnight, resulting in a white suspension. The solids were isolated by filtration and dried for 4 hours at 50° C. to provide 161 mg of product (>99% yield). Purity by HPLC was determined to be 99.5% and by NMR to be >95%.

(ii) Substitution of isopropyl acetate for isopropyl alcohol in method (i) afforded a white suspension after stirring overnight. The solids were isolated by filtration and dried for 4 hours at 50° C. to provide 168 mg of product (>99% yield). Purity by HPLC was determined to be 99.8% and by NMR to be >95%.

Substitution of isopropyl acetate for tetrahydrofuran in method (i) afforded a white suspension after stirring overnight. The solids were isolated by filtration and dried for 4 hours at 50° C. to provide 161 mg of product (>99% yield). Purity by HPLC was determined to be 99.4% and by NMR to be >95%.

Analysis by x-ray powder diffraction, showed the products of each of methods 9i) to (iii) to be the same, which was labelled Pattern A.

Stage 3b: Preparation of DMT Fumarate

To a 5 L flange flask under $N_2$ was charged fumaric acid (152.7 g, 1.315 mol) and Stage 2 (248.2 g, 1.315 mol) as a solution in ethanol (2928 ml). The mixture was heated to 75° C. to give a dark brown solution. The solution was polish filtered into a preheated (80° C.) 5 L jacketed vessel. The solution was then cooled to 70° C. and seeded with Pattern A (0.1 wt %), the seed was allowed to mature for 30 minutes before cooling to 0° C. at a rate of 5° C./hour. After stirring for an additional 4 hours at 0° C., the batch was filtered and washed with cold ethanol (496 ml×2) and then dried at 50° C. overnight. This provided 312.4 g (yield=78%) of Stage 3 in a purity of 99.9% by HPLC and >95% by NMR. XRPD: Pattern A.

Synthesis of Deuterated Mixtures of DMT Compounds

A modified synthesis at stage 2 using solid $LiAlH_4/LiAlD_4$ mixtures was adopted, using 1.8 equivalents of $LiAlH_4/LiAlD_4$ versus 0.9 equivalents using the process described above for undeuterated DMT.

Six deuteration reactions were performed.

Representative Synthesis of a Deuterated Mixture (Using 1:1 $LiAlH_4:LiAlD_4$) of DMT Compounds To a 250 ml 3-neck flask under $N_2$ was charged $LiAlH_4$ (1.013 g, 26.7 mmol), $LiAlD_4$ (1.120 g, 26.7 mmol) and THF (100 ml). The resultant suspension was stirred for 30 minutes before stage 1 (6 g, 29.666 mmol) was charged portion-wise over 15 minutes at 20-40° C. The reaction mixture was then heated to reflux (66° C.) for 2 hours where HPLC indicated no stage 1 remained. The mixture was cooled to 0° C. and quenched with 25% Rochelle's salts (aq) (120 ml) over 30 minutes at <30° C. The resultant milky suspension was stirred for 1 hour and then allowed to separate. The lower aqueous layer was removed and the upper organic layer washed with saturated brine (30 ml). The organics were then dried over $MgSO_4$, filtered and concentrated in vacuo. This provided 4.3 g of crude material. The crude was then taken up in ethanol (52 ml) and charged with fumaric acid (2.66 g, 22.917 mmol) before heating to 75° C. The resultant solution was allowed to cool to ambient temperature overnight before further cooling to 0-5° C. for 1 hour. The solids were isolated by filtration and washed with cold ethanol (6.5 ml×2). The filtercake was dried at 50° C. overnight to provided 5.7 g (yield=63%) of product in a purity of 99.9% by HPLC and >95% by NMR.

Assessment of Extents of Deuteration

This was achieved by LCMS-SIM (SIM=single ion monitoring), the analysis giving a separate ion count for each mass for the three deuterated N,N-dimethyltryptamine compounds (N,N-dimethyltryptamine (DO), α-protio, α-deutero-N,N-dimethyltryptamine (D1) and α,α-dideutero-N,N-dimethyltryptamine (D2)) at the retention time for N,N-dimethyltryptamine. The percentage of each component was then calculated from these ion counts.

For example, % D0=[D0/(D0+D1+D2)]×100.

HPLC Parameters

| System: | Agilent 1100/1200 series liquid chromatograph or equivalent |
| --- | --- |
| Column: | Triart Phenyl; 150 × 4.6 mm, 3.0 μm particle size (Ex: YMC, Part Part number: TPH12S03-1546PTH) |
| Mobile phase A: | Water: Trifluoroacetic acid (100:0.05%) |
| Mobile phase B: | Acetonitrile : Trifluoroacetic acid (100:0.05%) |
| Gradient: | Time %A %B |
| | 0 95 5 |
| | 13 62 38 |
| | 26 5 95 |
| | 30.5 5 95 |
| | 31 95 5 |
| Flow rate: | 1.0 ml/min |
| Stop time: | 31 minutes Post runtime: 4 minutes |
| Injection volume: | 5 μL Wash vial: N/A |
| Column temperature: | 30° C. combined |
| Wavelength: | 200 nm, (4 nm) Reference: N/A |

Mass Spectrometry Parameters

| System: | Agilent 6100 series Quadrupole LC-MS or equivalent | | | | | |
| --- | --- | --- | --- | --- | --- | --- |
| Drying gas flow: | 12.0 L/min | | | Drying gas temp.: | 350° C. | |
| Nebuliser pressure: | 35 psig | | | | | |
| Fragmentor: | 110 | | | | Gain: 1.00 | |

| Cpd | RT | RRT | Conc | Diluent | Detection | Mass |
| --- | --- | --- | --- | --- | --- | --- |
| D0 | 10.64 | 1.00 | 0.30 mg/ml | $CH_3CN:H_2O$ (50:50) | (+) SIM | 189.10 m/z |
| D1 | 10.64 | 1.00 | 0.30 mg/ml | $CH_3CN:H_2O$ (50:50) | (+) SIM | 190.10 m/z |
| D2 | 10.64 | 1.00 | 0.30 mg/ml | $CH_3CN:H_2O$ (50:50) | (+) SIM | 191.10 m/z |

MS-SIM range is the target mass ± 0.1 m/z

The data for the six deuterated reactions are tabulated in Table 1 below:

TABLE 1

In vitro intrinsic clearance of DMT (SPL026) and 6 deuterated compound blends

| Mixture No. (LiAlH$_4$:LiAlD$_4$ ratio) | Input (stage 1) | Output stage 3 (yield) | Purity by HPLC | Purity by NMR | Deuteration % D0 | D1 | D2 |
|---|---|---|---|---|---|---|---|
| 1 (SPL026) (0:1) | 5 g | 5.3 g (65%) | 99.7% | >95% | 0.7% | 2.7% | 96.6% |
| 2 (1:1) | 6 g | 5.699 g (63%) | 99.9% | >95% | 30.0% | 48.3% | 21.7% |
| 3 (1:2) | 5 g | 4.206 g (52%) | 99.9% | >95% | 16.5% | 46.8% | 36.8% |
| 4 (1:3) | 5 g | 5.558 g (68%) | 99.8% | >95% | 9.3% | 41.5% | 49.2% |
| 5 (2:1) | 5 g | 4.218 g (52%) | 99.9% | >95% | 47.5% | 41.3% | 11.2% |
| 6 (3:1) | 5 g | 5.0 g (62%) | 99.4% | >95% | 57.5% | 35.3% | 7.4% |

In vitro determination of intrinsic clearance is a valuable model for predicting in vivo hepatic clearance. The liver is the main organ of drug metabolism in the body, containing both phase I and phase II drug metabolising enzymes, which are present in the intact cell.

Aim

To use human hepatocytes to assess the in vitro intrinsic clearance of deuterated DMT analogue blends relative to DMT.

Description of the Experiment

Human (mixed gender) hepatocytes pooled from 10 donors (0.545 million cells/ml) were used to investigate the in vitro intrinsic clearance of DMT and 6 deuterated analogues.

A concentration of 5 µM was used for all test compounds, as well as sumatriptan, serotonin, benzylamine controls. This concentration was chosen in order to maximise the signal-to-noise ratio, while remaining under the Michaelis constant (Km) for the monoamine oxidase enzyme (MAO). Diltiazem and diclofenac controls were used at a laboratory-validated concentration of 1 µM.

Test compounds were mixed with the hepatocyte suspension within a 96-well plate and incubated for up to 60 minutes at 37° C. The suspension was continuously agitated. At 7 time points, small aliquots were withdrawn, and the test compound/blend concentration therein was measured by LC-MS/MS. The time points measured were 2, 4, 8, 15, 30, 45 and 60 minutes.

The following LC-MS/MS conditions were used for the analysis:

| | |
|---|---|
| Instrument: | Thermo TSQ Quantiva with Thermo Vanquish UPLC system |
| Column: | Luna Omega 2.1 × 50 mm 2.6 µm |
| Solvent A: | H$_2$ + 0.1% formic acid |
| Solvent B: | Acetonitrile + 0.1% formic acid |
| Flow rate: | 0.8 ml/min |
| Injection vol: | 1 µl |
| Column temp: | 65° C. |
| Gradient: | Time (mins) / % Solvent B |
| | 0.00 / 5.0 |
| | 0.90 / 75.0 |
| | 1.36 / 99.0 |
| | 1.36 / 5.0 |
| | 1.80 / 5.0 |

MS Parameters:

| | |
|---|---|
| Positive ion spray voltage: | 4000 V |
| Vaporiser temperature: | 450° C. |
| Ion transfer tube temp: | 365° C. |
| Sheath gas: | 54 |
| Aux gas: | 17 |
| Sweep gas: | 1 |
| Dwell time | 8 ms |

MRM Transitions:

D0=mass to charge ratio 189.14>58.16.

D1=mass to charge ratio 190.14>59.17.

D2=mass to charge ratio 191.14>60.17.

The MRM transitions were determined from a preliminary analysis of DMT samples containing either no deuterium (for D0 transition), or high levels of either D1 or D2 deuteration (for the D1 and D2 transitions respectively).

The resulting concentration-time profile was then used to calculate intrinsic clearance (CLint) and half-life (t ½). To do this, the MS peak area or MS peak area/IS response of each analyte is plotted on a natural log scale on the y axis versus time (min) of sampling on the X axis. The slope of this line is the elimination rate constant. This is converted to a half-life by −ln(2)/slope. Intrinsic clearance is calculated from the slope/elimination rate constant and the formula is CLint=(−1000*slope)/cell density in 1E6 cells/ml, to give units of microlitre/min/million cells.

Intrinsic clearance and half-life values were calculated for DMT and the 6 deuterated mixtures described above. These data were weighted dependent on the ratio of D0, D1 and D2 to give an overall intrinsic clearance and half-life value for each compound blend (Table 2A).

TABLE 2A

In vitro intrinsic clearance and calculated half-life of DMT and 6 deuterated mixtures

| Compound name or Mixture No (per Table 1) | LiAlH$_4$:LiAlD$_4$ input ratio | D$_0$:D$_1$:D$_2$ output ratio | Molecular weight | Intrinsic clearance (µL/min/million cells) | Half-life (min) |
|---|---|---|---|---|---|
| DMT (SPL026) | 1:0 | 100:0:0 | 188.269 | 13.77 | 92.39 |
| i | 0:1 | 0.7:2.7:96.6 | 190.240 | 7.15 | 178.79 |
| ii | 1:1 | 30.0:48.3:21.7 | 189.192 | 10.46 | 125.80 |
| iii | 1:2 | 16.5:46.8:36.8 | 189.669 | 9.36 | 140.43 |
| iv | 1:3 | 9.3:41.5:49.2 | 189.676 | 11.14 | 116.84 |
| v | 2:1 | 47.5:41.3:11.2 | 188.910 | 10.99 | 119.61 |
| vi | 3:1 | 57.4:35.3:7.4 | 188.961 | 13.64 | 95.04 |

Data were fitted with a linear model using regression analysis, which revealed that deuterium enrichment at the α-carbon of DMT decreases intrinsic clearance linearly with increasing molecular weight (MW), therefore enabling manufacture of DMT drug substances with half-lives which can be accurately predicted in the range identified.

Mixture 1, which contains 96.6% D2-DMT, sees the biggest change, with the intrinsic clearance rate almost halved compared to undeuterated-DMT (FIG. 2), nearly doubling the half-life (FIG. 1). Intermediate blends of deuteration (Mixtures 2 to 5) decreased intrinsic clearance in a manner correlated with molecular weight (FIG. 2).

Use of Liver Mitochondrial Fraction to Model Human Metabolism of Deuterated DMT

Given the predicted 5 minute half-life of DMT in humans, the inventors expect that DMT is largely broken down before reaching the human liver. Therefore, an alternative in vitro assay was selected as a more appropriate system to model human metabolism of DMT.

The following assays conducted on Human Liver Mitochondrial (HLMt) fractions predict enhanced fold-change between SPL026 and D2-deuterated SPL028i compared with the fold-change predicted in hepatocyte studies.

In vitro determination of the intrinsic clearance of SPL026, SPL028i, SPL028ii, SPL028iii, SPL028vii and SPL028viii were assessed in two separate experimental assays. 1 µM of all test compounds were added separately to 0.5 mg/mL of human liver mitochondrial fraction. 5 µM of MAO-A substrate Serotonin and MAO-B substrate Benzylamine were added as positive controls and confirmed the presence of MAO-A and MAO-B.

which increased with increasing level of $D_2$-deuteration. These data support the observation that deuteration of the methyl groups and alpha carbon of $D_8$-deuterated SPL028viii exerts a synergistic effect, rather than an additive effect.

In terms of half-life, alpha carbon deuteration ($D_2$, SPL028i) exerted a 10.3 fold change in half-life relative to un-deuterated DMT (SPL026), whereas methyl group deuteration ($D_6$, SPL028vii) exerted a 1.2 fold change. One may expect that both alpha carbon and methyl group deuteration in $D_8$ (SPL028viii) to exert an additive effect. However, results revealed a 14.5 fold change in half-life, leaving a 3-fold unaccounted for. This finding suggests that alpha carbon and methyl group deuteration of DMT exerts a synergistic effect in the hinderance of DMT clearance.

Example 5

Preparation of a Powder for Injection (PFI) of N,N-dimethyltryptamine fumarate (SPL026)

Development of Formulation

A stable formulation isotonic with human blood serum and suitable for intravenous (IV) bolus administration of DMT fumarate was developed. These formulations were prepared and placed under accelerated storage to assess stability over several weeks. Following analysis, the drug product was lyophilized for storage as a powder for injection.

All stated concentrations below are expressed in terms of the free base (i.e. in the absence of fumarate counterion). To

TABLE 2B

Intrinsic clearance and half-life of SPL026, SPL028i, SPL028ii, SPL028iii, SPL027vii and SPL028viii in human liver mitochondrial fraction.

| Compound Name | Half-life (min) | | | | | Fold change from SPL026 |
|---|---|---|---|---|---|---|
| | R1 | R2 | R3 | R4 | Mean | |
| SPL026 | 8.8 | 8.4 | 7.6 | 8.3 | 8.3 | 1.0 |
| SPL028i | 86.1 | 99.4 | 82.6 | 72.1 | 85.0 | 10.3*** |
| SPL028ii | — | — | 28.0 | 30.7 | 29.4 | 3.5*** |
| SPL028iii | 31.5 | 30.7 | 34.7 | 35.0 | 33.0 | 4.0*** |
| SPL028vii | — | — | 9.4 | 10.9 | 10.2 | 1.2 |
| SPL028viii | 121.4 | 133.9 | 92.9 | 131.5† | 119.9 | 14.5*** |
| Benzylamine | 24.3 | 22.1 | 21.2 | 23.5 | 22.8 | |
| Serotonin | 9.3 | 9.1 | 9.1 | 8.5 | 9.0 | |

†Note
for compound SPL028viii, replicate 4 (R4): compound levels remain consistent for initial 15 minutes before decreasing. All time-points included in the intrinsic clearance calculation.
*indicate $p < 0.05$; and
***$p < 0.001$ significant difference from SPL026.

Half-life increased and intrinsic clearance decreased with increasing level of deuteration for the SPL028 compounds, when compared to SPL026. An independent welch's t-test was performed to detect the clearance change relative to SPL026 for each test compound separately. All compounds, except for SPL028vii saw a significant change in half-life and intrinsic clearance compared to SPL026.

$D_8$-deuterated SPL028viii saw the greatest change in half-life (14.5-fold increase) and intrinsic clearance (14.2-fold change) relative to SPL026. 96.6% $D_2$-deuterated SPL028i also showed a large change in half-life and clearance (14.3- and 14.2-fold change, respectively) compared to SPL026. Intermediate $D_2$-deuterated blends: 21.7% $D_2$-deuterated SPL028ii; 36.8% $D_2$-deuterated SPL028iii saw a less significant change in clearance and half-life from SPL028, do so, a correction factor of 1.59 has been applied to the specific batch of drug substance as supplied. Any compound selected from N,N-dimethyltryptamine and its deuterated analogues, and pharmaceutically acceptable salts of these compounds may be formulated according to the methods outlined in this example. Solid dosage forms of N, N-dimethyltryptamine fumarate formulated as a powder for injection may be used as a baseline against which to benchmark bioavailability, or by proxy half-life, of solid dosage forms of the present invention.

Experimental Details
Initial Tests

Solubility of DMT fumarate was assessed at a concentration of 10 mg/ml in a small selection of aqueous vehicles (water, saline, 20 mM phosphate buffer and a combination of buffer and saline).

Phosphate buffer (100 ml) was prepared using 219.53 mg of the dibasic form [HPO$_4$][Na]$_2$ with 183.7 mg of the monobasic form [H$_2$PO$_4$]Na, both dihydrate salts. The solution was adjusted to pH 7.0 with addition of NaOH (1 M) and then made to volume. 10 ml of a 10 mg/ml formulation was prepared.

A phosphate buffer combined with saline was initially tested (20 mM phosphate buffer in 0.45% w/v saline) as a good starting point for a physiologically acceptable formulation with no solubility issues. To prepare this, sodium chloride was first dissolved in water to produce the saline solution (100 ml, 0.45% w/v). The phosphate salts, in the quantities described above, were then dissolved in the saline solution and the pH was adjusted using NaOH (1 M).

DMT fumarate was readily soluble in each aqueous vehicle. In terms of appearance, each solution was a clear beige colour, which on filtration (using 0.2 μm filters) was removed to produce a clear colourless solution. The pH of these solutions was in the range 3-4.

Buffer strength at 30 and 50 mM (as phosphate buffer, pH 7.4, prepared in 0.45% w/v sodium chloride) was tested to assess the effect of the buffer on pH control of formulations comprising concentrations of 2 or 2.5 mg/ml DMT fumarate. This buffer strength range was chosen in order to determine the required buffer strength so as to fix the pH of the formulation to about pH 7.4. When developing formulations for injection, it is typical to match the pH of the formulation with those of the patient's blood serum. Human blood serum has a pH of about 7.4. The buffers were prepared as follows. Saline solution was prepared by dissolving 9 g of sodium chloride in 2 litres of water. The phosphate salts (e.g. 30 mM=dibasic dihydrate (4.29 g), monobasic dihydrate (1.43 g), 50 mM=dibasic dihydrate (7.28 g), monobasic dihydrate (2.25 g)) were dissolved into the saline solution the pH was adjusted to 7.4 using NaOH (1 M). 9 g of NaCl in 2 litres of water. pH adjustment to pH 7.4 with 1M NaOH.

The initial pH of each solution following preparation was less than pH 7.4. At 20 mM the initial pH value of 5.9 continued to drop on storage of the solution overnight in the laboratory, indicating that the buffering capacity of the buffer at 20 mM concentration was insufficient. At both 30 mM and 50 mM buffer strengths, the initial pH values were >6.5 and remained stable.

A short-term stability assessment was performed and data obtained for the pH, osmolality and assay are presented in Tables 3 and 4. The data in Table 4 were obtained on storage of the formulations at between 40 to 50° C.

TABLE 3

Short-term formulation stability assessment

| Sample | pH | | | | Osmolality (mOsm/kg) | | | | Assay (mg/ml) | | | |
|---|---|---|---|---|---|---|---|---|---|---|---|---|
| | Initial | 24 hr | Day 5 | Day 7 | Initial | 24 hr | Day 5 | Day 7 | Initial | 24 hr | Day 5 | Day 7 |
| 2 mg · ml$^{-1}$/30 mM buffer/light$^a$ | 6.74 | 6.74 | — | 6.71 | 239 | 238 | — | 244 | 2.00 | 2.02 | — | 2.09 |
| 2 mg · ml$^{-1}$/30 mM buffer/dark$^b$ | 6.74 | 6.73 | — | 6.72 | 239 | 235 | — | 253 | — | 1.99 | — | 2.05 |
| 2 mg · ml$^{-1}$/30 mM buffer/2-8° C. | 6.74 | 6.73 | — | 6.72 | 239 | 238 | — | 237 | 1.99 | 1.96 | — | 2.09 |
| 2 mg · ml$^{-1}$/50 mM buffer/light$^a$ | 6.95 | 6.96 | — | 6.95 | 285 | 284 | — | 289 | 1.95 | 1.99 | — | 2.04 |
| 2 mg · ml$^{-1}$/50 mM buffer/dark$^b$ | 6.85 | 6.98 | — | 6.95 | 285 | 285 | — | 286 | — | — | — | 2.04 |
| 2 mg · ml$^{-1}$/50 mM buffer/2-8° C. | 6.95 | 6.97 | — | 6.95 | 285 | 284 | — | 283 | 1.98 | 1.98 | — | 2.08 |
| 2.5 mg · ml$^{-1}$/50 mM buffer/light$^a$ | 6.87 | — | 6.86 | — | 288 | — | 286 | — | 2.46 | — | 2.51 | — |
| 2.5 mg · ml$^{-1}$/50 mM buffer/dark$^b$ | 6.87 | — | 6.86 | — | 288 | — | 287 | — | 2.43 | — | 2.60 | — |
| 2.5 mg · ml$^{-1}$/50 mM buffer/2-8° C. | 6.87 | — | 6.86 | — | 288 | — | 288 | — | — | — | 2.57 | — |

$^{a,b}$Light and dark at laboratory temperature storage (15-25° C.)

TABLE 4

Short-term formulation stability assessment

| Sample | pH | | Assay (mg/ml) | | Related Substances (%) | |
|---|---|---|---|---|---|---|
| | Initial | Day 7 | Initial | Day 7 | Initial | Day 7 |
| 2.5 mg/ml/50 mM buffer | 6.88 | 6.87 | 2.49 | 2.38 | N.D < 0.02 | 1.13 |
| 2.5 mg/ml/50 mM buffer (N$_2$ sparged) | 6.88 | 6.87 | 2.49 | 2.55 | N.D < 0.02 | N.D < 0.02 |
| 2.5 mg/ml/50 mM buffer (2-8° C.) | 6.88 | 6.89 | 2.49 | 2.53 | N.D < 0.02 | N.D < 0.02 |
| 2.5 mg/ml/50 mM buffer (UV light exposure) | 6.83 | — | 2.10 | — | 3.57 | — |
| 2.5 mg/ml/50 mM buffer (UV light exposure Control) | 6.84 | — | 2.50 | — | N.D < 0.02 | — |

Noticeably, the go-to buffers stored under ambient conditions (1 week at 40° C.), without $N_2$ sparging or control of UV light exposure, contained 1.13% of related substances after 1 week of storage. This is compared to the related substances formed under the same conditions for Britton-Robinson buffered formulations below.

Development of Formulation

Materials

Details of the DMT fumarate employed for stability purposes are provided in Table 5 and excipients used are listed in Table 6.

TABLE 5

DMT fumarate used for the stability study

| Material | Batch Number | Supplier |
|---|---|---|
| DMT fumarate | SPL026 | Onyx Scientific, Sunderland |

TABLE 6

Excipients used for the formulation development study

| Material | Batch Number | Supplier |
|---|---|---|
| Purified water | Not applicable | Elga dispenser, asset number ARC37642 |
| Sodium chloride | 17D194102 | VWR |
| di-Sodium hydrogen orthophosphate dihydrate | 1997160 | Fisher Chemicals |
| Sodium dihydrogen orthophosphate dihydrate | 1724808 | Fisher Chemicals |
| Volumetric 1M sodium hydroxide solution | 726144 | Scientific Laboratory Supplies |
| Glacial acetic acid | 1727841 | Fisher Chemicals |

Equipment

Equipment, excluding standard laboratory glassware, used throughout the studies is listed in Table 7. Calibration and verification of equipment were performed in accordance with standard operating procedures for all measurements, as required.

TABLE 7

Typical equipment used during the formulation development study

| Item | Make and Model | Asset Number |
|---|---|---|
| Balance | Mettler Toledo, MX5 | 32721 |
| Balance | Sartorius, ME215S | 31476 |
| Single Stir Plate | Bibby HB502 | 20234 |
| pH Meter | Mettler Toledo, MP225 | 20322 |
| Osmolality | Advanced Instruments Osmo 1 | 38564 |
| Filters | Millex MP PES 0.22 μm | n/a |
| Light Box | Heraeus SunTest | 28 694 |

Osmolality Readings

Osmolality readings were obtained using an Advanced Instruments Osmo1 instrument. A single sample syringe was used to introduce the sample into the osmometer, which employed the industry-preferred principles of freezing point depression to determine osmolality accurately and precisely.

Instrument verification was performed using 50, 850 and 2000 mOsm/kg $H_2O$ calibration standards prior to analysis, for confirmation of accuracy.

pH Readings pH readings were obtained using a Mettler Toledo MP225 pH meter. The electrode probe was inserted into the test solutions, contained in a glass vial, with brief stirring at ambient temperature.

Instrument verification was performed prior and post each use using, as supplied, pH buffer solutions over the range pH 1.68 to 10.01 for confirmation of accuracy.

High Performance Liquid Chromatography (HPLC)

The following HPLC parameters were employed to assess assays and the quantity of related substances (substances resulting from DMT fumarate degradation) of solutions of DMT fumarate that were prepared as part of the formulation development.

| Column: | YMC-Triart Phenyl; 150 × 4.6 mm, 3 μm, | | |
|---|---|---|---|
| Mobile phase A: | Water:Trifluoroacetic acid (100:0.05 v/v) | | |
| Mobile phase B: | Acetonitrile:Trifluoroacetic acid (100:0.05 v/v) | | |
| Diluent: | Acetonitrile:Water (50:50) | | |
| Gradient timetable: | Time (min) | % A | % B |
| | 0.0 | 95 | 5 |
| | 13.0 | 62 | 38 |
| | 26.0 | 5 | 95 |
| | 30.5 | 5 | 95 |
| | 31.0 | 95 | 5 |
| Flow rate: | 1.0 ml.min$^{-1}$ | | |
| Column temperature: | 30° C. | | |
| Injection volume: | 7.5 μL | | |
| Needle wash: | Water:Acetonitrile (50:50) | | |
| Seal Wash: | Water:Acetonitrile (50:50) | | |
| Run time: | 35 minutes | | |
| Detection Wavelength: | 220 nm | | |

Formulation Development

The solubility of DMT fumarate was initially assessed over a range of different pH values, from pH 4 to pH 10. Formulations were then prepared at the target concentration of 2.5 mg/ml of DMT fumarate over a pH range of pH 4 to pH 9.

Solubility of DMT Fumarate at Different pH Values

Seven solutions, each containing a concentration of 20 mg/ml of DMT fumarate were prepared in Britton-Robinson (B-R) buffer solution. On dissolution of DMT fumarate in each test formulation (DMT fumarate was very soluble, needing only swirling and shaking in each), the pH of each test formulation was then adjusted to pH 4, 5, 6, 7, 8 and 9 using sodium hydroxide solution.

Solubility of a concentration of 20 mg/ml of DMT fumarate was confirmed at pH 4, 5, 6 and 7—these solutions were clear and colourless. The sample at pH 8 was hazy and the samples at pH 9 and pH 10 contained a precipitate. Following overnight storage under ambient conditions, the pH of each solution was measured and the results showed no changes from the initial pH values. Each sample was then filtered and analysed for content. Each solution, including the high pH solutions where precipitate was present, contained approximately the same content of DMT fumarate.

pH Stability pH-stability of DMT fumarate at a concentration of 2.5 mg/ml was assessed in 40 mM Britton-Robinson buffer solution over the buffer solution range pH 4 to 9 (nominal). The pH of each formulation was measured at preparation, following 7 days storage at 40° C. and then further storage over an additional 3 days at 40° C. and 7 days at 50° C. (so a total further storage of 10 days). Analysis of these formulations was performed on preparation, and then after 7 and 17 days storage for content (assay) and related substances.

Two extra aliquots of the pH 7 (nominal) solution were taken for additional testing, one was sparged with nitrogen and the second was stressed under intense UV light for 4 hours equivalent to 1 ICH unit (200 watt hours UVA, 0.6 million luxhours).

On preparation of each formulation, there was a drop in pH in the range of 0.14 units (pH 4 formulation) to 1.29 units (pH 9 formulation) this being due to the acidic nature of the drug substance. Once prepared, the pH of each formulation remained stable at the two subsequent stability time points (Table 8).

The concentration of DMT fumarate was determined by HPLC at preparation and on the two subsequent stability occasions (Table 9). All results confirmed accurate preparation with no significant concentration changes on either Day 7 or Day 17. The only significant change over the course of the experiment was a drop in concentration following light stressing of the aliquot of the nominal pH 7 formulation. This was accompanied by a significant increase in observed degradants.

In terms of related substances, only peaks greater than 0.05% of the total peak area have been reported. The summarised related substances data are presented in Table 10, with individual values in Table 11 (7 days storage at 40° C.) and Table 12 (10 days storage at 40° C. with a further 7 days storage at 50° C.).

At preparation, no related substances peaks were present. On Day 7 only the pH 9 formulation contained a peak at a relative retention time of 1.11. With only minimal additional peaks observed following the 7 days elevated storage, the formulations were further stressed (with an increase in storage temperature over time) and on analysis after 17 days storage, additional peaks were present in several of the formulations with a clear trend visible with increasing numbers of peaks and peak area with increasing pH, ranging from no peaks (pH 4) to 3 peaks with a total peak area of 0.61% (pH 9). The nitrogen sparged formulation (pH 7) was significantly more robust than its unsparged equivalent confirming that oxidation is a degradation pathway. The light stressed formulation was the most degraded sample with a total related substances value of 1.68%.

TABLE 8 pH-stability measurement for SPL026 in Britton-Robinson buffer

| Nominal pH | Initial | Day 7[b] | Day 17[c] |
|---|---|---|---|
| 4.0 | 3.86 | 3.84 | 3.84 |
| 5.0 | 4.57 | 4.55 | 4.52 |
| 6.0 | 5.08 | 5.07 | 5.06 |
| 6.5 | 5.33 | 5.33 | 5.31 |
| 7.0 | 6.12 | 6.10 | 6.10 |
| 6.5 sparged $N_2$ | 6.12 | 6.18 | 6.09 |
| 7.0 UV Light | 6.07[a] | — | — |
| 7.5 | 6.60 | 6.58 | 6.59 |
| 8.0 | 6.87 | 6.86 | 6.84 |
| 9.0 | 7.71 | 7.72 | 7.70 |

[a] pH on completion of testing
[b] 7 days storage at 40° C.
[c] 10 days storage at 40° C. followed by 7 days at 50° C.

TABLE 9 pH-stability for SPL026 in Britton-Robinson buffer (assay)

| Nominal pH | Concentration (mg.ml$^{-1}$) | | | |
|---|---|---|---|---|
| | Initial | Day 7[b] | Day 17[c] | Light |
| 4.0 | 2.47 | 2.57 | 2.52 | – |
| 5.0 | 2.50 | 2.48 | 2.52 | – |
| 6.0 | 2.51 | 2.56 | 2.48 | – |
| 6.5 | 2.49 | 2.59 | 2.51 | – |
| 7.0 | 2.54 | 2.54 | 2.45 | – |
| 7.0 sparged $N_2$ | 2.54 | 2.54 | 2.51 | – |
| 7.0 UV Light | 2.54 | – | – | 2.26[a] |
| 7.5 | 2.50 | 2.55 | 2.46 | – |
| 8.0 | 2.49 | 2.49 | 2.42 | – |
| 9.0 | 2.47 | 2.41 | 2.46 | – |

[a] concentration on completion of light stressing (200 watt hours UVA, 0.6 million luxhours). This sample was an aliquot of the pH 7 solution
[b] 7 days storage at 40° C.
[c] 10 days storage at 40° C. followed by 7 days at 50° C.

TABLE 10 pH stability total related substances assay for SPL026 in Britton-Robinson buffer

| Nominal pH | Total related substances (%) | | | |
|---|---|---|---|---|
| | Initial | Day 7[b] | Day 17[c] | Light |
| 4.0 | ND | ND | ND | — |
| 5.0 | ND | ND | 0.07 | — |
| 6.0 | ND | ND | 0.09 | — |
| 6.5 | ND | ND | 0.10 | — |
| 7.0 | ND | ND | 0.26 | — |
| 7.0 sparged $N_2$ | ND | ND | 0.05 | — |
| 7.0 UV Light | ND | — | — | 1.68a |
| 7.5 | ND | ND | 0.42 | — |
| 8.0 | ND | ND | 0.58 | — |
| 9.0 | ND | ND | 0.61 | — |

ND-<0.02 area of total peak area
[a] % related substances on completion of light stressing (200 watt hours UVA, 0.6 million luxhours). This sample was an aliquot of the pH 7 solution
[b] 7 days storage at 40° C.
[c] 10 days storage at 40° C. followed by 7 days at 50° C.

TABLE 11 pH stability individual related substances assay for SPL026 in Britton-Robinson buffer, 7 days storage at 40° C.

Relative retention time and percentage area of total peak area (peaks > 0.05% of total peak area)

| Nominal pH | Day[a] | 0.54 | 0.62 | 0.64 | 0.73 | 0.74 | 0.77 | 0.80 | 0.81 | 0.91 | 0.95 | 1.06 | 1.10 | 1.11 | 1.17 | 1.20 | 1.56 |
|---|---|---|---|---|---|---|---|---|---|---|---|---|---|---|---|---|---|
| 4 | 7 | — | — | — | — | — | — | — | — | — | — | — | — | — | — | — | — |
| 5 | 7 | — | — | — | — | — | — | — | — | — | — | — | — | — | — | — | — |
| 6 | 7 | — | — | — | — | — | — | — | — | — | — | — | — | — | — | — | — |
| 6.5 | 7 | — | — | — | — | — | — | — | — | — | — | — | — | — | — | — | — |
| 6.5 with $N_2$[a] | 7 | — | — | — | — | — | — | — | — | — | — | — | — | — | — | — | — |
| 7 UV light[b] | n/a[c] | 0.05 | 0.17 | 0.54 | 0.23 | 0.15 | 0.06 | 0.07 | — | — | — | — | — | — | 0.18 | 0.13 | 0.10 |
| 7 | 7 | — | — | — | — | — | — | — | — | — | — | — | — | — | — | — | — |
| 7.5 | 7 | — | — | — | — | — | — | — | — | — | — | — | — | — | — | — | — |
| 8 | 7 | — | — | — | — | — | — | — | — | — | — | — | — | — | — | — | — |
| 9 | 7 | — | — | — | — | — | — | — | — | — | — | — | — | — | — | — | — |

[a]Sparged with nitrogen
[b]UV light exposure (200 watt hours UVA, 0.6 million luxhours)
[c]Subsample of the pH 7 formulation

TABLE 12 pH stability individual related substances assay for SPL026 in Britton-Robinson buffer, 10 days storage at 40° C., 7 days storage at 50° C.

Relative retention time and percentage area of total peak area (peaks > 0.05% of total peak area)

| Nominal pH | Day[a] | 0.54 | 0.62 | 0.64 | 0.73 | 0.74 | 0.77 | 0.80 | 0.81 | 0.91 | 0.95 | 1.06 | 1.10 | 1.11 | 1.17 | 1.20 | 1.56 |
|---|---|---|---|---|---|---|---|---|---|---|---|---|---|---|---|---|---|
| 4 | 17 | — | — | — | — | — | — | — | — | — | — | — | — | — | — | — | — |
| 5 | 17 | — | — | — | — | — | — | — | — | — | — | — | — | — | — | — | 0.07 |
| 6 | 17 | — | — | — | — | — | — | — | — | — | — | — | — | — | — | — | 0.09 |
| 6.5 | 17 | — | — | — | — | — | — | — | — | — | — | — | — | — | — | — | 0.10 |
| 6.5 with $N_2$[a] | 17 | — | — | — | — | — | — | — | — | — | — | — | — | — | — | — | 0.05 |
| 7 | 17 | — | — | — | 0.09 | — | — | — | — | 0.05 | — | — | — | — | — | — | 0.12 |
| 7.5 | 17 | — | — | — | 0.14 | — | — | — | — | 0.07 | — | — | — | 0.12 | — | — | 0.09 |
| 8 | 17 | — | — | — | 0.15 | — | — | — | — | 0.09 | 0.05 | — | — | 0.22 | — | — | 0.07 |
| 9 | 17 | — | — | — | 0.12 | — | — | — | — | 0.11 | — | — | — | 0.12 | — | — | 0.38 |

[a]Sparged with nitrogen

Comparison of Stability of Initial Formulation with B-R Buffered Formulations

As described above, N,N-dimethyltryptamine fumarate formulations comprising the go-to buffer stored at temperatures of 40 to 50° C., without $N_2$ sparging or control of UV light exposure, contained 1.13% of related substances after 1 week of storage. The amounts of related substances that formed in the go-to formulation and the B-R formulations on storage for a week at 40 to 50° C. are compared in Table 13. DMT fumarate formulations comprising B-R buffers stored under the same conditions contained less than 0.02% of related substances after 1 week of storage (>5.7× fewer related substances than the go-to formulation) suggesting a greater stability of the B-R formulations.

As described above, when developing formulations for injection, it is typical to match the pH of the formulation with those of the patient's blood serum. Human blood serum has a pH of about 7.4. Consequently, the obvious go-to formulation of salts of optionally substituted dimethyltryptamine compounds is one with a pH of 7.4. A greater stability of formulations of such salts prepared at pH values of 7.0 or less was unexpected.

TABLE 13

Short-term formulation stability assessment of go-to formulation and formulations of the invention

| Sample | pH Initial | pH Day 7 | Assay (mg/ml) Initial | Assay (mg/ml) Day 7 | Related Substances (%) Initial | Related Substances (%) Day 7 |
|---|---|---|---|---|---|---|
| 2.5 mg/ml/50 mM phosphate buffered saline, pH 7.4 (go-to formulation) | 6.88 | 6.87 | 2.49 | 2.38 | N.D < 0.02 | 1.13 |
| 2.5 mg/ml/40 mM B-R buffer, pH 4.0 (non-obvious formulation) | 3.86 | 3.84 | 2.47 | 2.57 | N.D < 0.02 | N.D < 0.02 |
| 2.5 mg/ml/40 mM B-R buffer, pH 5.0 (non-obvious formulation) | 4.57 | 4.55 | 2.50 | 2.48 | N.D < 0.02 | N.D < 0.02 |

TABLE 13-continued

Short-term formulation stability assessment of go-to formulation and formulations of the invention

| Sample | pH Initial | pH Day7 | Assay (mg/ml) Initial | Assay (mg/ml) Day 7 | Related Substances (%) Initial | Related Substances (%) Day 7 |
|---|---|---|---|---|---|---|
| 2.5 mg/ml/40 mM B-R buffer, pH 6.0 (non-obvious formulation) | 5.08 | 5.07 | 2.51 | 2.56 | N.D < 0.02 | N.D < 0.02 |
| 2.5 mg/ml/40 mM B-R buffer, pH 6.5 (non-obvious formulation) | 5.33 | 5.33 | 2.49 | 2.59 | N.D < 0.02 | N.D < 0.02 |
| 2.5 mg/ml/40 mM B-R buffer, pH 7.0 (non-obvious formulation) | 6.12 | 6.10 | 2.54 | 2.54 | N.D < 0.02 | N.D < 0.02 |

Candidate Formulation Development

From the results of the pH stability assessment the decision was made to fix the formulation pH at pH 4.0 (after storage for a week, the B-R formulation at pH 4.0 contained no peaks corresponding to related substances, suggesting that this was the most stable formulation) and to assess the use of phosphate and acetate buffer systems at concentrations of 20 mM and 40 mM, as these both buffer well at the optimal pH for stability, and assess both sodium chloride and dextrose as tonicity agents.

Formulation Preparation

Details of each individual formulation (numbered 1 to 8) are presented in Table 14 and Table 15. For each formulation, the requisite acid and tonicity agent was dissolved in 80 ml of water. The pH of this solution was then adjusted to pH 4 (±0.5) with 1 M sodium hydroxide solution. The drug substance was then dissolved, the pH adjusted to pH 4 (±0.1) with more 1 M sodium hydroxide solution and then made to volume with water and final pH check and adjusted as required. For each formulation, the volume of sodium hydroxide used was documented. The composition of each formulation is presented below in Table 14 (saline) and Table 15 (dextrose). Solvent (water) volumes may be adjusted to facilitated subsequent lyophilization, which may be facilitated by addition of one or more bulking agent, e.g. mannitol.

Stability Analysis

An aliquot of each formulation was taken for assay/related substances and osmolality check. The remainder of each formulation was filtered (filter size 0.2 μm) into a clear glass multi-dose vial, sparged with nitrogen, capped and placed into storage (60° C.) for 14 days. The 40 mM phosphate/dextrose formulation (formulation 8) was split into two aliquots with one aliquot stored in an amber glass multi-dose vial and one aliquot in a clear glass multi-dose vial.

TABLE 14

Candidate SPL026 formulation preparations (saline)
Saline Formulations

| | Formulation Number | | | |
|---|---|---|---|---|
| Ingredient | 1 | 2 | 3 | 4 |
| SPL026 | 398 mg | 398 mg | 398 mg | 398 mg |
| Acetic acid | 120 mg (20 mM) | 240 mg (40 mM) | — | — |
| Ortho-phosphoric acid (85%) | — | — | 231 mg (20 mM) | 461 mg (40 mM) |
| Sodium chloride | 780 mg | 720 mg | 780 mg | 720 mg |
| Sodium hydroxide | 38.8 mg | 60.8 mg | 103.2 mg | 185.6 mg |
| Volume prepared (ml) | 100 | 100 | 100 | 100 |

TABLE 15

Candidate SPL026 formulation preparations (dextrose)
Dextrose Formulations

| | Formulation Number | | | |
|---|---|---|---|---|
| Ingredient | 5 | 6 | 7 | 8 |
| SPL026 | 398 mg | 398 mg | 398 mg | 398 mg |
| Acetic acid | 120 mg (20 mM) | 240 mg (40 mM) | — | — |
| Ortho-phosphoric acid (85%) | — | — | 231 mg (20 mM) | 461 mg (40 mM) |
| Dextrose | 4300 mg | 3900 mg | 4300 mg | 3900 mg |
| Sodium hydroxide | 27.6 | 47.2 | 96.4 mg | 175.2 mg |
| Volume prepared (ml) | 100 | 100 | 100 | 100 |

Results

Concentration, osmolality and pH results for formulations at preparation and following storage at 60° C. are presented in Table 16. Related substances results following storage are presented in Table 17.

All formulations on preparation were clear colourless solutions. No related substances were present in any of the formulations following preparation.

Following removal from storage all formulations in terms of their appearance were no longer colourless but had acquired to varying degrees a hint of beige but all remained clear, colour was most pronounced in formulation 5 (20 mM acetate buffer/dextrose) which had the greatest concentration of related substances.

Osmolality and pH were confirmed as stable for each tested formulation with no significant changes.

Total related substances as peaks of more than 0.05% of total peak area ranged between 0.07% up to 0.52%. These data would suggest that for SPL026 saline is the preferred tonicity agent over dextrose.

All Day 14 results for the 40 mM phosphate/dextrose formulation stored in amber glass mirrored the clear glass results confirming that clear glass/amber glass storage has no impact on stability in terms of these storage conditions but given the previously noted light instability amber glass should be used as the primary pack.

TABLE 16

Candidate SPL026 formulation results, assay, osmolality and pH

| No. | Vehicle composition | Concentration (mg·ml⁻¹) Day 0 | Concentration (mg·ml⁻¹) 14 days, 60° C. | Osmolality (mOsm/kg) Day 0 | Osmolality (mOsm/kg) 14 days, 60° C. | pH Day 0 | pH 14 days, 60° C. |
|---|---|---|---|---|---|---|---|
| 1 | 20 mM acetate/saline | 2.50 | 2.52 | 305 | 300 | 3.94 | 3.94 |
| 2 | 40 mM acetate/saline | 2.54 | 2.54 | 307 | 318 | 3.98 | 4.01 |
| 3 | 20 mM phosphate/saline | 2.55 | 2.54 | 315 | 319 | 4.01 | 4.02 |
| 4 | 40 mM phosphate/saline | 2.53 | 2.46 | 330 | 347 | 4.00 | 3.99 |
| 5 | 20 mM acetate/dextrose | 2.50 | 2.46 | 300 | 308 | 3.97 | 4.05 |
| 6 | 40 mM acetate/dextrose | 2.51 | 2.47 | 304 | 310 | 4.02 | 4.06 |
| 7 | 20 mM phosphate/dextrose | 2.55 | 2.51 | 320 | 320 | 4.02 | 4.04 |
| 8 | 40 mM phosphate/dextrose | 2.58 | 2.48 | 339 | 336 | 4.01 | 4.04 |
| 8[a] | 40 mM phosphate/dextrose | — | 2.49 | — | 334 | — | 4.02 |

[a] stored in amber glass

TABLE 17

Related substances assay for candidate SPL026 formulations following storage at 60° C. for 14 days

| | RRT and percentage area of total peak area of peaks > 0.05% of total peak area | | | | | | |
|---|---|---|---|---|---|---|---|
| No. | 0.62 | 0.72 | 0.80 | 0.91 | 1.60 | 1.61 | Total |
| 1 | — | — | — | — | — | 0.11 | 0.11 |
| 2 | — | — | — | — | — | 0.08 | 0.08 |
| 3 | — | — | — | — | — | 0.09 | 0.09 |
| 4 | — | — | — | — | — | 0.07 | 0.07 |
| 5 | 0.05 | 0.05 | 0.07 | 0.07 | 0.08 | 0.20 | 0.52 |
| 6 | — | — | — | — | — | 0.13 | 0.13 |
| 7 | — | — | — | 0.05 | — | 0.16 | 0.21 |
| 8 | — | — | — | 0.05 | — | 0.15 | 0.20 |
| 8[a] | — | — | — | 0.07 | — | 0.23 | 0.30 |

[a] stored in amber glass

Example 6

Solid Oral Dosage Forms of α,α-dideutero-N,N-dimethyltryptamine (SPL028i)

Formulation (a)

| Capsule | | | |
|---|---|---|---|
| Ingredient/Component | ~% w/w | Unit Quantity | Reference |
| SPL028i as fumarate salt: | 45 | 98 | In-house |
| (free base equivalent): | (28) | (61 mg) | |
| Dicalcium phosphate: | 50 | 108 mg | Ph.Eur |
| Sodium lauryl sulphate: | 5 | 10 mg | Ph.Eur |
| Coni-Snap ® Size 3 hard gelatin capsule or Vcap ® Size 3 HPMC capsule: | — | One | In-house |
| Total: | — | 216 mg | |

Formulation (b)

| Capsule | | | |
|---|---|---|---|
| Ingredient/Component | ~% w/w | Unit Quantity | Reference |
| SPL028i as fumarate salt | 73 | 138 mg | In-house |
| (free base equivalent): | (45) | (86 mg) | |
| Starch | 25 | 47 mg | Ph.Eur |
| Colloidal silica | 2 | 4 mg | Ph.Eur |
| Coni-Snap ® Size 3 hard gelatin capsule or Vcap ® Size 3 HPMC capsule | — | One | In-house |
| Total | — | 189 mg | |

Formulation (c)

| Capsule | | | |
|---|---|---|---|
| Ingredient/Component | ~% w/w | Unit Quantity | Reference |
| SPL028i as free base | 93 | 200 mg | In-house |
| Microcrystalline cellulose | 6 | 13 mg | Ph.Eur |
| Colloidal silica | 1 | 3 mg | Ph.Eur |
| Coni-Snap ® Size 3 hard gelatin capsule or Vcap ® Size 3 HPMC capsule | — | One | In-house |
| Total | — | 216 mg | |

Formulation (d)

| Capsule | | | |
|---|---|---|---|
| Ingredient/Component | ~% w/w | Unit Quantity | Reference |
| SPL028i as fumarate salt: | 36 | 77 | In-house |
| (free base equivalent): | (22) | (48 mg) | |
| Dicalcium phosphate: | 60 | 130 mg | Ph.Eur |
| Sodium lauryl sulphate: | 4 | 9 mg | Ph.Eur |
| Coni-Snap ® Size 3 hard gelatin capsule or Vcap ® Size 3 HPMC capsule: | — | One | In-house |
| Total: | — | 216 mg | |

Formulation (e)

| Capsule | | | |
|---|---|---|---|
| Ingredient/Component | ~% w/w | Unit Quantity | Reference |
| SPL028i as fumarate salt: | 86 | 185 mg | In-house |
| (free base equivalent): | (53) | (115 mg) | |
| Starch | 13 | 28 mg | Ph.Eur |

-continued

| Capsule | | | |
|---|---|---|---|
| Ingredient/Component | ~% w/w | Unit Quantity | Reference |
| Colloidal silica | 1 | 3 mg | Ph.Eur |
| Coni-Snap ® Size 3 hard gelatin capsule or Vcap ® Size 3 HPMC capsule | — | One | In-house |
| Total | — | 216 mg | |

Formulation (f)

| Tablet | | | |
|---|---|---|---|
| Ingredient/Component | ~%w/w | Unit Quantity | Reference |
| SPL028i as fumarate salt: (free base equivalent): | 49 (30) | 98 (61 mg) | In-house |
| Pregelatinised starch: | 35 | 70 mg | Ph.Eur |
| Calcium carbonate: | 10 | 20 mg | Ph.Eur |
| Crospovidone: | 4 | 8 mg | Ph.Eur |
| Stearic acid | 2 | 4 mg | Ph.Eur |
| Total: | — | 200 mg | |

Formulation (g)

| Tablet | | | |
|---|---|---|---|
| Ingredient/Component | ~%w/w | Unit Quantity | Reference |
| SPL028i as fumarate salt: (free base equivalent): | 69 (43) | 138 (86 mg) | In-house |
| Microcrystalline cellulose: | 28 | 56 mg | Ph.Eur |
| Colloidal Silica: | 2 | 4 mg | Ph.Eur |
| Magnesium stearate: | 1 | 2 mg | Ph.Eur |
| Total: | — | 200 mg | |

Formulation (h)

| Tablet | | | |
|---|---|---|---|
| Ingredient/Component | ~%w/w | Unit Quantity | Reference |
| SPL028i as a fumarate salt: (free base equivalent): | 38 (24) | 76 (47 mg) | In-house |
| Pregelatinised starch: | 46 | 92 mg | Ph.Eur |
| Calcium carbonate: | 10 | 20 mg | Ph.Eur |
| Crospovidone: | 4 | 8 mg | Ph.Eur |
| Stearic acid | 2 | 4 mg | Ph.Eur |
| Total: | — | 200 mg | |

Formulation (i)

| Tablet | | | |
|---|---|---|---|
| Ingredient/Component | ~%w/w | Unit Quantity | Reference |
| SPL028i as a fumarate salt: (free base equivalent): | 92 (57) | 184 (114 mg) | In-house |
| Microcrystalline cellulose: | 5 | 10 mg | Ph.Eur |
| Colloidal Silica: | 2 | 4 mg | Ph.Eur |
| Magnesium stearate: | 1 | 2 mg | Ph.Eur |
| Total: | — | 200 mg | |

Example 7

An in vivo investigation of the pharmacokinetic profile of N,N-dimethyltryptamine (DMT, SPL026), α,α,-dideutero-N,N-dimethyltryptamine analogue blends (SPL028i), and α,α,-dideutero-N,N-bis-trideuterio-dimethyltryptamine (SPL028viii) following oral dosing was performed in rats.

All scientific procedures on living animals conducted in the United Kingdom (UK) are subject to legislation under the Animals (Scientific Procedures) Act 1986 (referred to subsequently as 'the Act' and amended by the ASPA Regulations 2012). The Act conforms to the European Directive 2010/63/EU and to the European Convention for the Protection of Vertebrate Animals Used for Experimental and Other Scientific Purposes (ETS123) Strasbourg, Council of Europe)). The Act is administered by the UK Home Office and provides for establishment designation, issue of project licenses for specified programmes of work and issue of personal licenses for individuals conducting procedures.

All studies were conducted in accordance with the Act, with UK Home Office Guidance on the implementation of the Act and with all applicable Codes of Practice for the care and housing of laboratory animals. As detailed within the Act, each establishment is required to operate a local Animal Welfare and Ethical Review Body (AWERB). This is intended to ensure animal use is carefully considered and fully justified. The AWERB also ensures that proper account is taken of all possibilities for reduction, refinement and/or replacement of animals used and that the highest practicable standards of accommodation and care are achieved.

Methods

Test Compounds

| | |
|---|---|
| Substance code | SPL026 |
| Chemical name | N,N-dimethyltryptamine (DMT) fumarate salt |
| Molecular weight | DMT fumarate: 304.34 (DMT 188.27) |

| | |
|---|---|
| Substance code | SPL028i |
| Chemical name | (96.6%) α,α,-dideutero-N,N-dimethyltryptamine fumarate salt |
| Molecular weight | d2-DMT fumarate salt: 306.31 (d2-DMT: 190.24) (weighted MW) |

| | |
|---|---|
| Substance code | SPL028viii |
| Chemical name | (96.7%) α,α,-dideutero-N,N-bis-trideutero-dimethyltryptamine fumarate salt |
| Molecular weight | d8-DMT fumarate: 312.35 (d8-DMT: 196.28) (weighted MW) |

Animal Specifications

Animals were obtained from Charles River Ltd (Margate, Kent, UK) according to the following specifications:

| | | Target range | | Number to be dosed |
|---|---|---|---|---|
| Species | Strain | Bodyweight (g) | Age (weeks) | Male |
| Rat | Sprague Dawley | 250 to 300 g | 7-9 | 9 M |

Housing and Husbandry

| | | |
|---|---|---|
| Environmental conditions | Temperature | 21° C. ± 2° C. |
| | Relative humidity | 45% to 65% |
| | Daily light cycle | 12 h fluorescent lighting and 12 h dark |
| | Temperature and relative humidity will be continuously recorded | |
| Equilibration period | Minimum period of 4 days prior to use | |
| Housing | Grouped (up to 4) in polypropylene cages with solid floors | |
| Identification | Unique number by tail marking with indelible ink | |
| Health | A health examination will occur on receipt and the health status will be monitored throughout the acclimatization period. Any animals considered unhealthy will be excluded from the study. The suitability of each animal for experimental use will be confirmed before use | |
| Diet | Name: | RM1 (E) SQC pelleted diet |
| | Supplier: | Special Diets Services, Witham, Essex, UK |
| | Availability: | ad libitum |
| | A diet analysis certificate for each batch used will be retained at Pharmaron UK Ltd. It is considered unlikely that any constituent of the diet will interfere with the study. Food will be available ad libitum for the duration of the study. | |
| Drinking water: | Type: | Domestic potable water. |
| | Availability: | ad libitum |
| | The water quality will be in compliance with the Water Supply (UK) Regulations (2000). Routine chemical and bacterial analyses are conducted periodically by the local water authority. It is considered unlikely that any constituent of the water will interfere with the study. | |

Dosing Regime

Animals were weighed the morning of dosing with doses being administered based on the bodyweight and the specified dose volume.

25 mg/kg doses of each compound were administered by oral gavage in separate animals. 25 mg/kg dose was chosen based on a calculated animal equivalent dose of human bolus IV, which was increased by a factor of 10 to account for the oral administration route.

| Compound | SPL026 | SPL028i | SPL028viii |
|---|---|---|---|
| Route and frequency | Single oral | Single oral | Single oral |
| Dose level (mg/kg) | 25 | 25 | 25 |

Blood Sampling

Following dosing, serial whole blood samples (ca. 200 μL) were collected into individual K₂EDTA treated containers from a lateral tail vein (not used for dosing) via an indwelling cannula.

Samples were collected at the following times post dose:

Pre-dose, 1, 5, 10, 15, 30, 45, 60, 120, and 180 minutes.

Blood samples were placed into a cooling block before being centrifuged at 10,000 g, 2 minutes at ca. 4° C. and the resultant plasma drawn off. Remaining blood pellets were discarded. Following collection of the final samples via tail vein animals will be sacrificed by a Schedule One method and frozen until disposal. All samples are stored at ca. −80° C.

Bioanalysis

The bioanalytical method used was fully validated at Pharmaron UK Ltd. The table below details the 3 methods that were qualified:

| Method Number | Calibration Standards & QC's prepared with | Internal Standard | Accurately Quantify | Semi Quantify |
|---|---|---|---|---|
| 1 | SPL026 (DMT) | SPL028vii (d6-deuterated DMT) | SPL026 (DMT) | IAA |
| 2 | SPL028i (d2-deuterated DMT) | SPL028viii (d8-deuterated DMT) | SPL028i (d2-deuterated DMT) | IAA |
| 4 | SPL028viii (d8-deuterated DMT) | SPL028i (d2-deuterated DMT) | SPL028viii (d8-deuterated DMT) | IAA |

Analytical Method

Concentrations of DMT, d2-DMT and d8-DMT were determined in the rat plasma samples using the qualified methods that has been validated in this study. The concentration of semi quantified metabolites were estimated through determination of metabolite peak area ratio in the sample to the quantified compound calibration curve (also determined using peak area ratio).

Results

Test Substance Plasma Pharmacokinetics

Mean pre-dose plasma concentration of all test compounds were below limit of quantification in all animals. There was a high variability in the PK profile of test compound animals both within and between test compound groups, as demonstrated in Tables 18-20.

TABLE 18

Measured SPL026 concentrations over time

| | Determined Concentration in ng/mL | | | |
|---|---|---|---|---|
| | SPL026 (DMT) | | | |
| Time Point | 1 M | 2 M | 3 M | Mean |
| Predose | BLQ | BLQ | BLQ | BLQ |
| 1 min | BLQ | BLQ | 0.391 | <0.3 |

TABLE 18-continued

Measured SPL026 concentrations over time

Determined Concentration in ng/mL

SPL026 (DMT)

| Time Point | 1 M | 2 M | 3 M | Mean |
|---|---|---|---|---|
| 5 min | BLQ | BLQ | 0.590 | <0.4 |
| 10 min | BLQ | 4.06 | 20.7 | <8.4 |
| 15 min | 0.763 | 19.9 | 25.7 | 15.5 |
| 30 min | 7.77 | 25.2 | 29.5 | 20.8 |
| 45 min | 18.0 | 18.5 | 28.6 | 21.7 |
| 60 min | 16.9 | 31.6 | 34.1 | 27.5 |
| 120 min | 13.7 | 11.7 | 16.9 | 14.1 |
| 180 min | 5.83 | 2.57 | 2.45 | 3.6 |

BLQ—Below the lower limit of quantification 0.310 ng/mL

TABLE 19

Measured SPL028i concentrations over time

Determined Concentration in ng/mL

SPL028i (DMT-d2)

| Time Point | 4 M | 5 M | 6 M | Mean |
|---|---|---|---|---|
| Predose | BLQ | BLQ | BLQ | BLQ |
| 1 min | BLQ | BLQ | BLQ | BLQ |
| 5 min | 0.865 | 5.85 | 0.688 | 2.5 |
| 10 min | 2.42 | 49.2 | 6.72 | 19.4 |
| 15 min | 7.46 | 34.3 | 19.0 | 20.3 |
| 30 min | 22.6 | 46.4 | 22.6 | 30.5 |
| 45 min | 22.6 | 33.1 | 43.7 | 33.1 |
| 60 min | 30.5 | 32.1 | 53.1 | 38.6 |
| 120 min | 38.0 | 18.7 | 49.3 | 35.3 |

TABLE 20

Measured SPL028viii concentrations over time

Determined Concentration in ng/mL

SPL028viii (DMT-d8)

| Time Point | 7 M | 8 M | 9 M | Mean |
|---|---|---|---|---|
| Predose | BLQ | BLQ | BLQ | BLQ |
| 1 min | BLQ | 19.8 | BLQ | <6.8 |
| 5 min | 14.9 | 3.11 | 0.506 | 6.2 |
| 10 min | 18.0 | 13.7 | 11.8 | 14.5 |
| 15 min | 20.5 | 20.3 | 36.2 | 25.7 |
| 30 min | 9.08 | 23.0 | 35.7 | 22.6 |
| 45 min | 5.90 | 21.7 | 40.0 | 22.5 |
| 60 min | 4.43 | 30.5 | 62.0 | 32.3 |
| 120 min | 13.5 | 31.6 | 63.8 | 36.3 |

Figure 3:
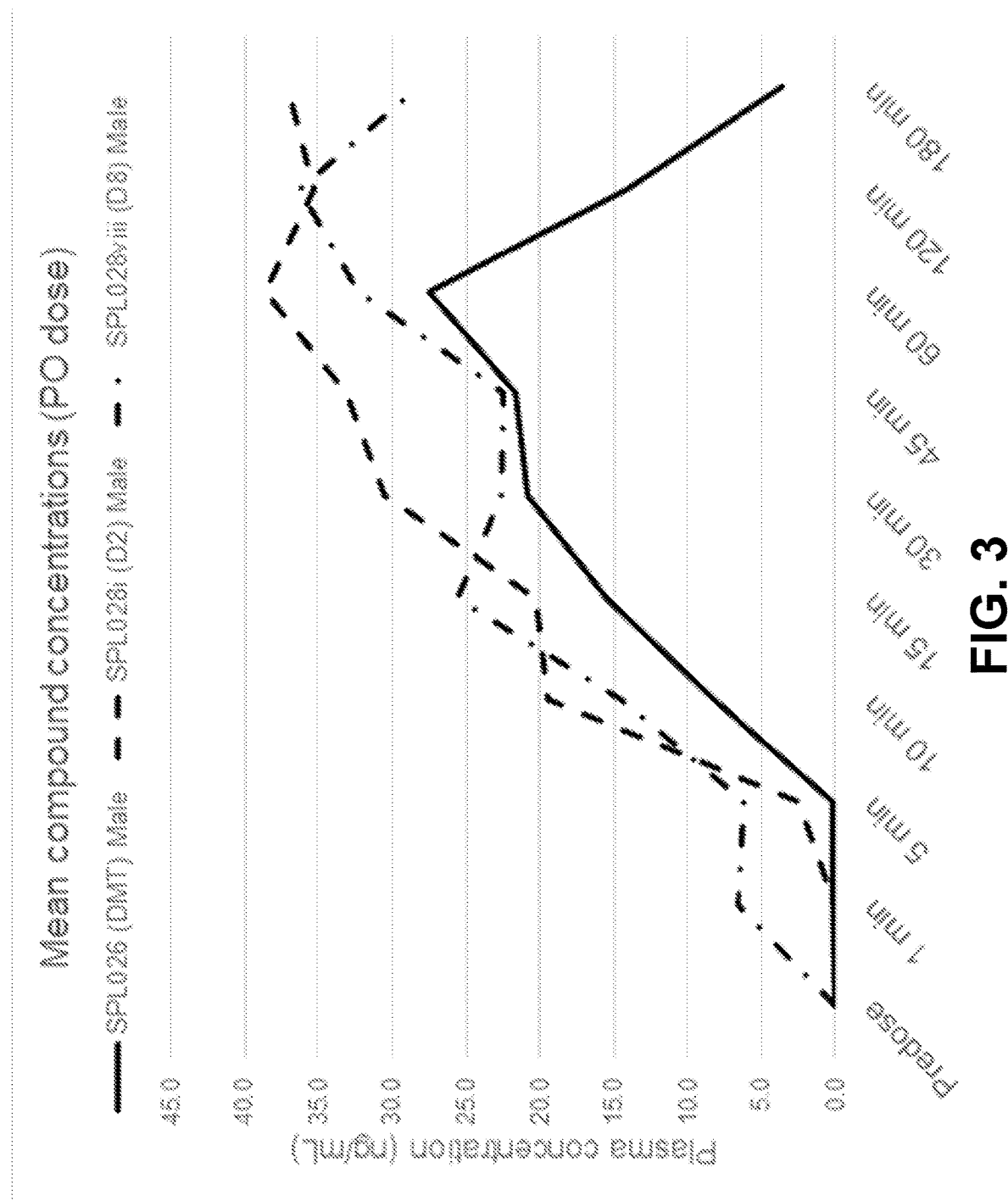
FIGS. 3 and 4 show in vivo metabolism of SPL026, SPL028i and SPL028viii in the rat following oral (PO (per os)) dosing. An increased systemic exposure of SPL028i and SPL028viii compared to SPL026 was observed.
Figure 4:
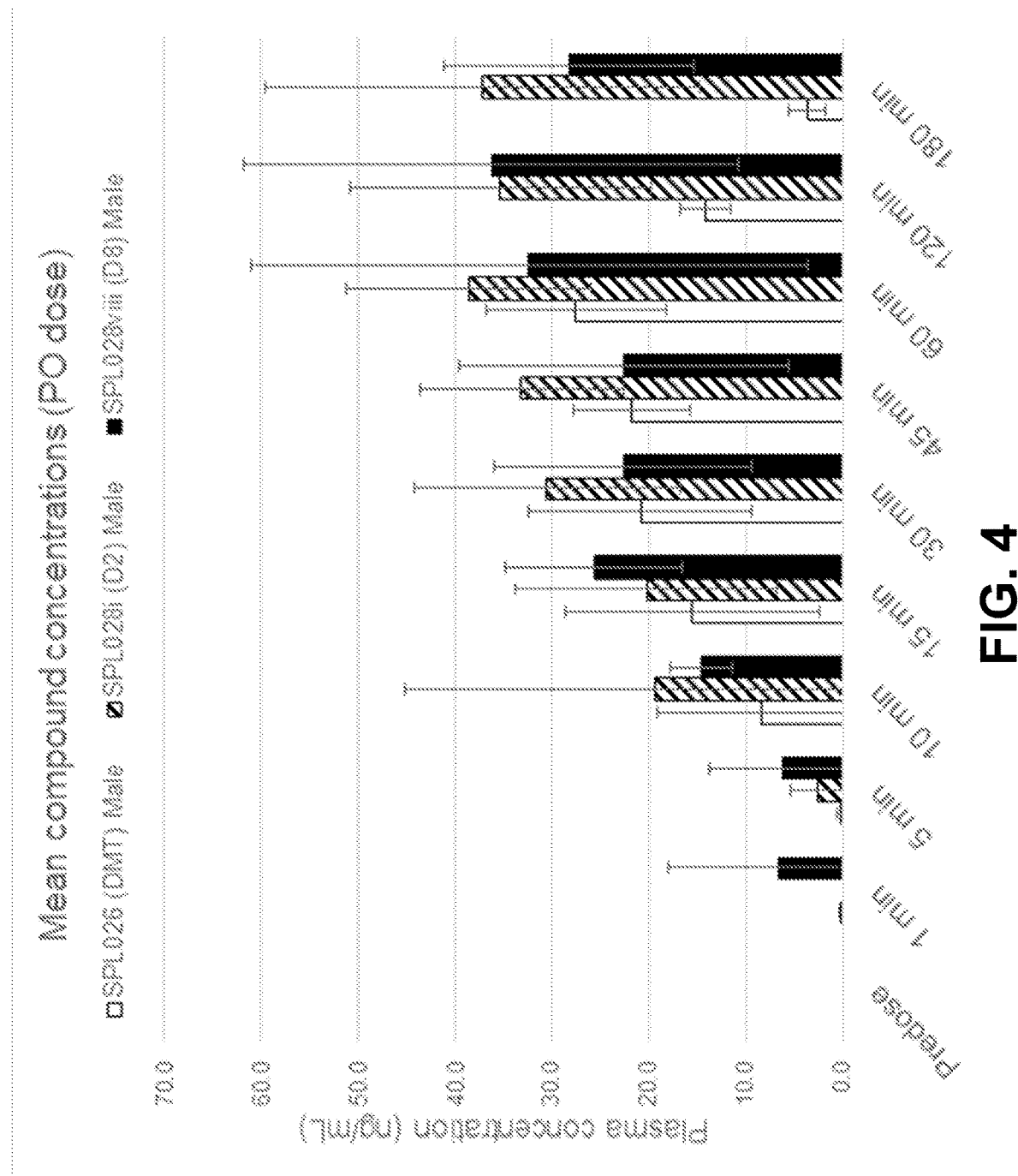
Figure 5:
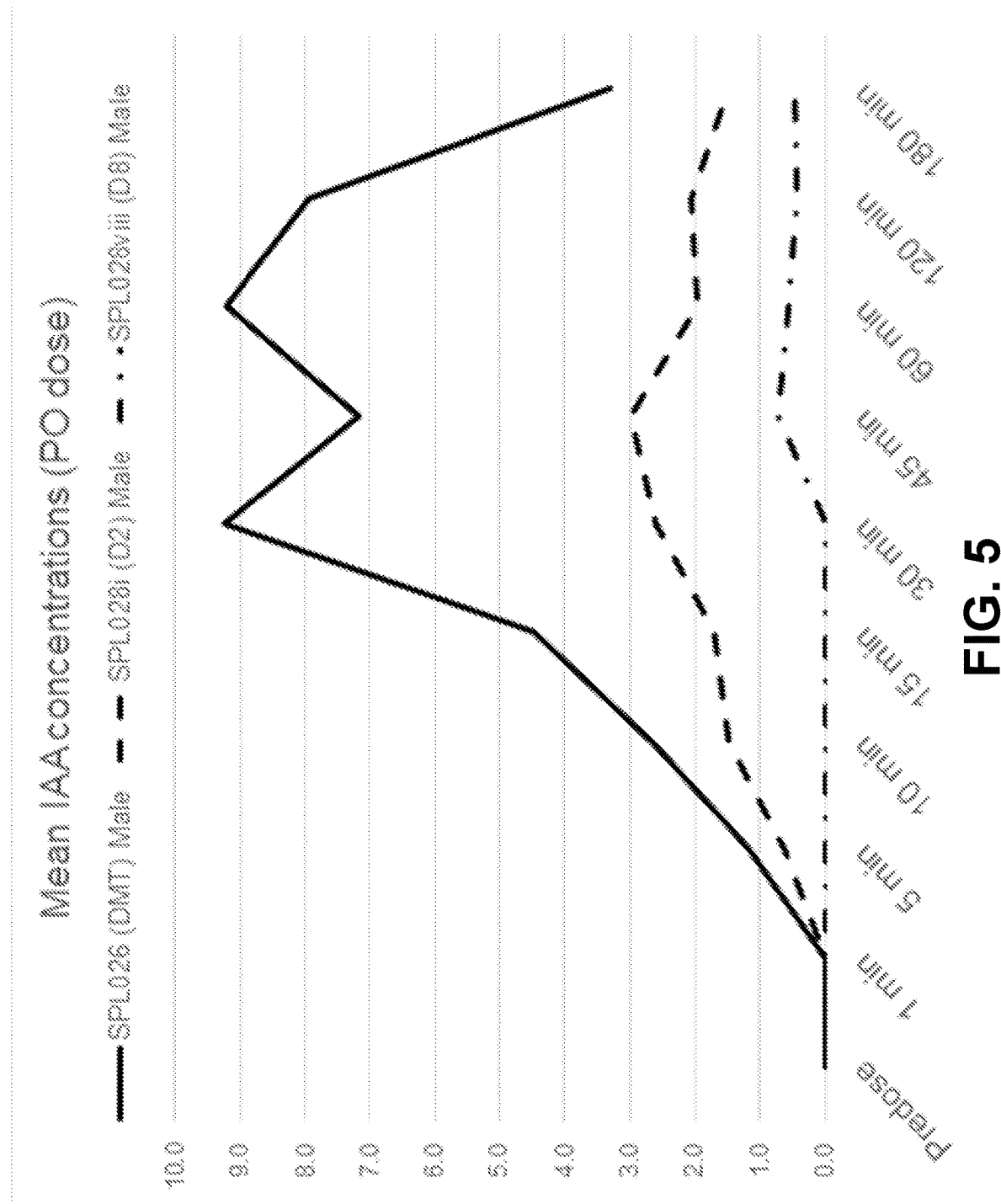
FIGS. 5 and 6 show in vivo biosynthesis of indole-3-Acetic Acid (IAA), the major metabolite of N,N-dimethyltryptamine, following PO dosing of SPL026, SPL028i and SPL028viii in the rat. A significant decrease in IAA biosynthesis following SPL028i and SPL028viii compared to SPL026 was observed.
Figure 6:
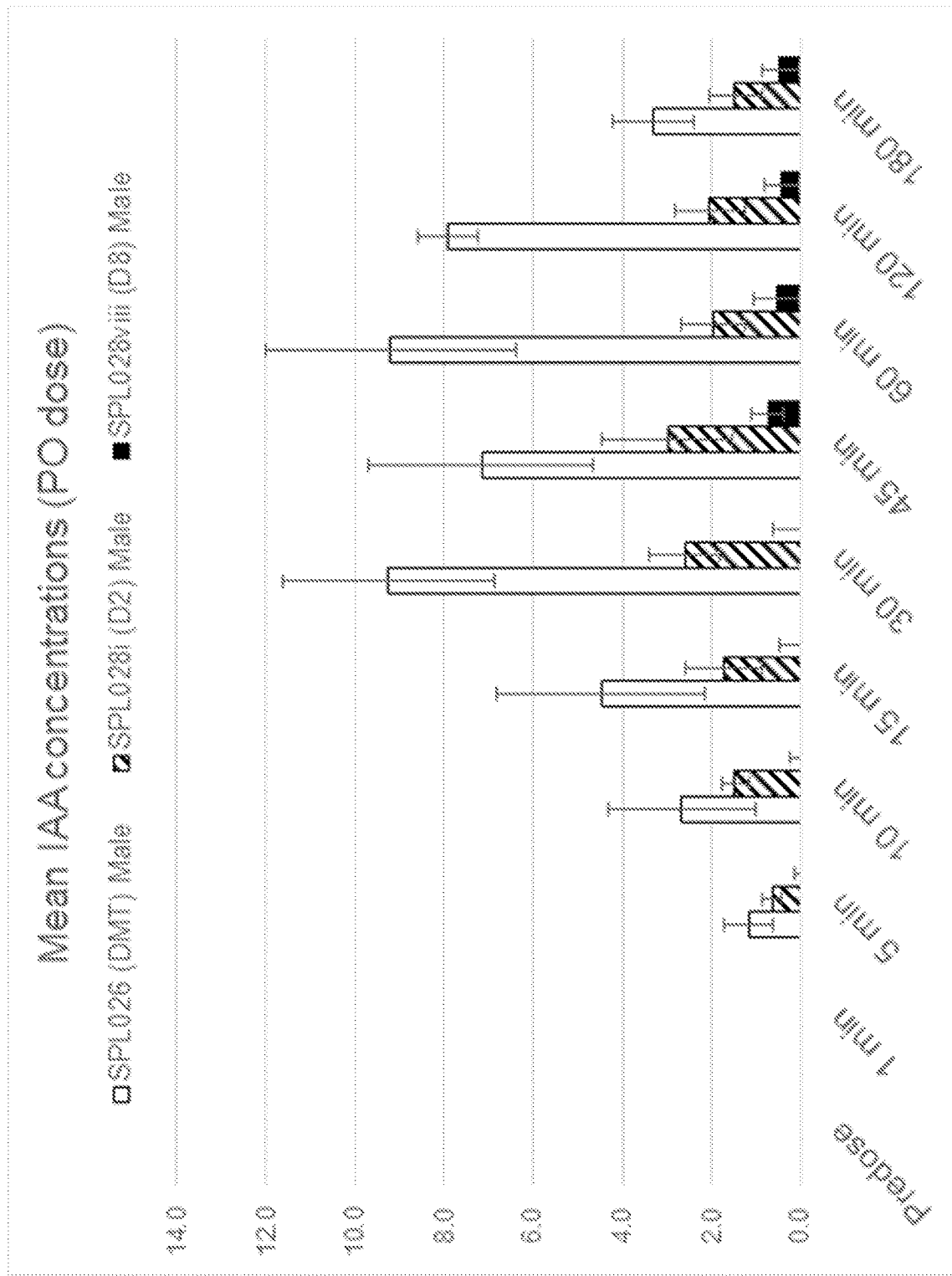

An increased systemic exposure of SPL028i and SPL028viii compared to SPL026 was observed. Deuteration was shown to have an effect of increasing mean tmax, mean Cmax and mean AUC(0-t) in both SPL028i and SPL028viii compounds compared to un-deuterated SPL026 (FIG. 3).

A ~1.95 and ~1.5-fold increase in mean Cmax was observed in SPL028i (54.3 ng/ml) and SPL028viii (40.77 ng/ml) groups when compared to SPL026 (27.9 ng/ml), respectively.

A ~2-fold increase in mean AUC(0-t) was observed in SPL028i (5923 h·ng/mL), and SPL208viii (5250 h·ng/mL) compound groups, when compared to SPL026.

IAA metabolite were significantly higher (p<0.05) in SPL026 dosed animals at all time points after 5 mins compared to SPL028viii group, and at all time points after 30 mins when compared to the SPL028i group.

Mean IAA tmax increased with increased deuteration of compounds, mean SPL026 tmax=30 min, SPL028i tmax=45 min, and SPL028viii tmax=60 min (Tables 21-23).

Mean IAA Cmax was ~11-fold higher in SPL026 (Cmax=9.204 ng/ml) compared to SPL028viii (Cmax=0.827 ng/ml) and ~3-fold higher when compared to SPL028i (Cmax=2.933) (Tables 21-23).

TABLE 21

Measured IAA concentrations over time after SPL026 administration

Estimated IAA Concentration in ng/mL

PO Dose (25 mg/kg)

SPL026 (DMT)

| Time Point | 1 M | 2 M | 3 M | Mean |
|---|---|---|---|---|
| Predose | BLQ | BLQ | BLQ | BLQ |
| 1 min | BLQ | BLQ | BLQ | BLQ |
| 5 min | 0.549 | 1.33 | 1.64 | 1.171 |
| 10 min | 1.08 | 2.58 | 4.39 | 2.683 |
| 15 min | 1.82 | 5.55 | 6.09 | 4.487 |
| 30 min | 7.08 | 11.8 | 8.88 | 9.245 |
| 45 min | 5.10 | 6.44 | 9.98 | 7.174 |
| 60 min | 6.18 | 9.74 | 11.7 | 9.204 |
| 120 min | 7.40 | 7.70 | 8.67 | 7.924 |
| 180 min | 4.34 | 2.53 | 3.08 | 3.316 |

TABLE 22

Measured IAA concentrations over time after SPL028i administration

Estimated IAA Concentration in ng/mL

PO Dose (25 mg/kg)

SPL028i (DMT-d2)

| Time Point | 4 M | 5 M | 6 M | Mean |
|---|---|---|---|---|
| Predose | BLQ | BLQ | BLQ | BLQ |
| 1 min | BLQ | BLQ | BLQ | BLQ |
| 5 min | 0.523 | 0.874 | 0.503 | 0.633 |
| 10 min | 1.24 | 1.84 | 1.34 | 1.473 |
| 15 min | 2.41 | 0.749 | 1.97 | 1.709 |
| 30 min | 3.53 | 2.10 | 2.18 | 2.606 |
| 45 min | 4.67 | 1.95 | 2.35 | 2.993 |
| 60 min | 2.78 | 1.59 | 1.50 | 1.955 |
| 120 min | 2.94 | 1.42 | 1.81 | 2.055 |
| 180 min | 2.09 | 0.898 | 1.45 | 1.480 |

TABLE 23

Measured IAA concentrations over time after SPL028viii administration

Estimated IAA Concentration in ng/mL

PO Dose (25 mg/kg)

SPL028viii (DMT-d8)

| Time Point | 7 M | 10 M | 7 M | Mean |
|---|---|---|---|---|
| Predose | BLQ | BLQ | BLQ | BLQ |
| 1 min | BLQ | BLQ | BLQ | BLQ |
| 5 min | BLQ | BLQ | 0.223 | <0.281 |
| 10 min | BLQ | BLQ | 0.430 | <0.350 |
| 15 min | BLQ | BLQ | 0.846 | <0.489 |
| 30 min | BLQ | 1.04 | BLQ | <0.544 |
| 45 min | 0.347 | 0.821 | 1.0 | 0.733 |

TABLE 23-continued

Measured IAA concentrations over time after SPL028viii administration

| | Estimated IAA Concentration in ng/mL | | | |
|---|---|---|---|---|
| | PO Dose (25 mg/kg) | | | |
| | SPL028viii (DMT-d8) | | | |
| Time Point | 7 M | 10 M | 7 M | Mean |
| 60 min | BLQ | 0.772 | 0.883 | 0.827 |
| 120 min | BLQ | 0.516 | 0.747 | 0.631 |
| 180 min | BLQ | 0.747 | 0.673 | 0.710 |

The results of this example confirm that deuteration of DMT in SPL028i and SPL028viii attenuates the metabolic degradation of compound in plasma relative to undeuterated SPL026 after oral administration in rats.

There was a high variability of PK profiles of animals both within and between test compound groups. This finding reflects the high inter-individual variability of DMT administration reported in human clinical studies (Kaplan, Mandel et al. 1974, Strassman and Qualls 1994).

Deuterium substitution of DMT increased the systemic exposure of compounds in animals, as measured through increased AUC, Cmax, and Tmax over the measured time course (0-180 mins). This finding is indicative of an increase in half-life and metabolic stability of compounds, which was also demonstrated in vitro mitochondrial fraction (see example 5). In contrast to in vitro results which demonstrated an increase in metabolic stability in SPL028viii relative to SPL028i (and potential synergistic effect between alpha and methyl group deuteration on drug stability), SPL028i had a higher AUC and Cmax compared to SPL028viii.

IAA, the most abundant metabolite of DMT, is formed via the oxidative deamination reaction by the MAO enzyme (Suzuki, Katsumata et al. 1981, Barker 2018). Deuteration of DMT was shown to significantly reduce the levels of IAA quantified after oral administration in vivo, which was more significant in SPL028viii than SPL028i, when compared to IAA levels after SPL026 administration. Lower plasma levels of IAA were detected after administration of SPL028viii (mean Cmax=0.827 ng/ml), compared to SPL028i (mean Cmax=2.993 ng/ml) indicates that increased deuteration increases the metabolic stability of DMT in an additive fashion, i.e. higher metabolic stability of SPL028viii>SPL028i. This result indicates that deuteration of DMT induces a deuterium kinetic isotope effect (DKIE) through the inhibition of MAO mediated metabolism, which is more pronounced with increased level of deuteration.

A comparison of PK profiles of SPL026, SPL028i, SPL028viii and IAA metabolites demonstrate a clear DKIE and increase in metabolic stability of deuterium enriched compounds (SPL028i, SPL028viii), when compared to SPL026. The longer tmax and lower levels of IAA metabolite measured in the SPL028viii group compared to SPL028i, indicate that metabolic stability and oral bioavailability is increased with increased level of deuteration.

The invention claimed is:

1. A solid dosage form comprising two or more compounds selected from N,N-dimethyltryptamine and its deuterated analogues and pharmaceutically acceptable salts thereof.

2. The solid dosage form of claim 1, wherein the deuterated analogues are selected from α,α-dideutero-N,N-dimethyltryptamine compounds and α-protio, α-deutero-N,N-dimethyltryptamine compounds.

3. The solid dosage form of claim 2, wherein the deuterated analogues are compounds of Formula I:

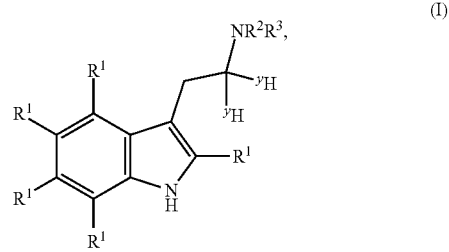

wherein:

each $R^1$ is independently selected from H and D;

$R^2$ is selected from $CH_3$ and $CD_3$;

$R^3$ is selected from $CH_3$ and $CD_3$;

each $^yH$ is independently selected from H and D; and the ratio of deuterium:protium in a compound of Formula I is greater than that found naturally in hydrogen, or pharmaceutically acceptable salts thereof.

4. The solid dosage form of claim 3, wherein each $R^1$ is H.

5. The solid dosage form of claim 3, wherein both $^yH$ are D.

6. The solid dosage form of claim 3, wherein both $R^2$ and $R^3$ are $CD_3$.

7. The solid dosage form of claim 3, comprising one or more compounds selected from Compounds 1 to 5, or a pharmaceutically acceptable salt thereof:

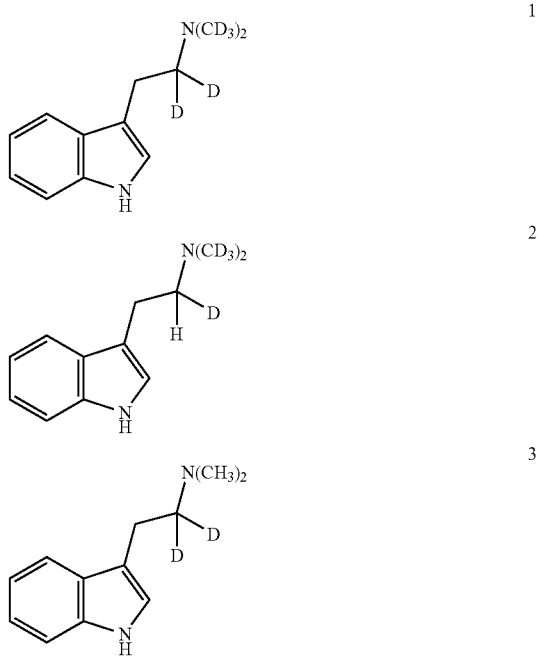

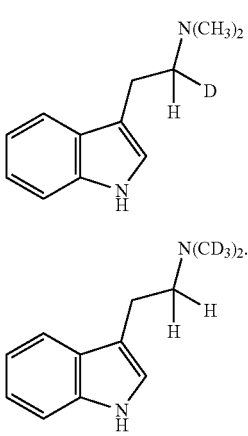

8. The solid dosage form of claim 1, comprising a combination of N,N-dimethyltryptamine and 2% or more by weight of one or more compounds selected from α,α-dideutero-N,N-dimethyltryptamine compounds, α-protio, α-deutero-N,N-dimethyltryptamine compounds and pharmaceutically acceptable salts of these compounds.

9. The solid dosage form of claim 1, comprising up to 50% by weight, based on the total solid dosage form, of one or more compounds selected from α,α-dideutero-N,N-dimethyltryptamine compounds, α-protio, α-deutero-N,N-dimethyltryptamine compounds and pharmaceutically acceptable salts thereof.

10. The solid dosage form of claim 1, comprising from 5% to 95% by weight of N,N-dimethyltryptamine or a pharmaceutically acceptable salt thereof.

11. The solid dosage form of claim 1, comprising from 5% to 95% by weight of an α,α-dideutero-N,N-dimethyltryptamine, or a pharmaceutically acceptable salt thereof.

12. The solid dosage form of claim 1, consisting essentially of two or more compounds selected from N,N-dimethyltryptamine, α-protio, α-deutero-N,N-dimethyltryptamine, and α,α-dideutero-N,N-dimethyltryptamine as biologically active agents, the solid dosage form optionally being in the form of a pharmaceutically acceptable salt, wherein the mean molecular weight of N,N-dimethyltryptamine, α-protio, α-deutero-N,N-dimethyltryptamine and α,α-dideutero-N,N-dimethyltryptamine present in the solid dosage form is less than or equal to 190.28 grams per mole.

13. The solid dosage form of claim 1, comprising an N,N-dimethyltryptamine compound in the form of a pharmaceutically acceptable salt, wherein the pharmaceutically acceptable salt is a fumarate salt.

14. The solid dosage form of claim 1, comprising an N,N-dimethyltryptamine compound in the form of a free-base.

15. A method of treating a psychiatric disorder or a neurological disorder, comprising:
administering to a patient in need thereof, the solid dosage form of claim 1.

16. The method of claim 15, wherein the psychiatric or neurological disorder is selected from the group consisting of (i) an obsessive compulsive disorder, (ii) a depressive disorder, (iii) a schizophrenia disorder, (iv) a schizotypal disorder, (v) an anxiety disorder, (vi) substance abuse, (vii) an avolition disorder, and (viii) a brain injury disorder.

17. The method of claim 15, wherein the psychiatric or neurological disorder is major depressive disorder.

18. The method of claim 15, wherein the psychiatric or neurological disorder is treatment resistant depression.

19. A method of treating a psychiatric disorder or a neurological disorder, comprising:
administering to a patient in need thereof, the solid dosage form of claim 10.

20. A method of treating a psychiatric disorder or a neurological disorder, comprising:
administering to a patient in need thereof, the solid dosage form of claim 13.

21. The solid dosage form of claim 1, consisting essentially of two or more compounds selected from N,N-dimethyltryptamine and its deuterated analogues and pharmaceutically acceptable salts thereof as biologically active agents.

* * * * *